US005871628A

United States Patent [19]
Dabiri et al.

[11] Patent Number: 5,871,628
[45] Date of Patent: Feb. 16, 1999

[54] AUTOMATIC SEQUENCER/GENOTYPER HAVING EXTENDED SPECTRAL RESPONSE

[75] Inventors: Ali Dabiri, San Diego, Calif.; Harold R. Garner, Flower Mound, Tex.

[73] Assignees: The University of Texas System, Austin, Tex.; Science Applications International Corporation, San Diego, Calif.

[21] Appl. No.: 702,767

[22] Filed: Aug. 22, 1996

[51] Int. Cl.⁶ .......................... G01N 27/26; G01N 27/447
[52] U.S. Cl. .......................... 204/461; 204/452; 204/603; 204/612
[58] Field of Search .................................... 204/603, 612, 204/452, 461

[56] References Cited

U.S. PATENT DOCUMENTS

| | | | |
|---|---|---|---|
| 4,892,638 | 1/1990 | Watanabe et al. | 204/612 |
| 5,069,769 | 12/1991 | Fujimiya et al. | 204/461 |
| 5,124,247 | 6/1992 | Ansorge | 435/6 |
| 5,171,534 | 12/1992 | Smith et al. | 204/612 |
| 5,192,412 | 3/1993 | Kambara et al. | 204/612 |
| 5,213,673 | 5/1993 | Fujimiya et al. | 204/612 |
| 5,246,866 | 9/1993 | Nasu et al. | 204/461 |
| 5,268,080 | 12/1993 | Kambara et al. | 204/461 |
| 5,290,419 | 3/1994 | Kambara et al. | 204/612 |
| 5,294,323 | 3/1994 | Togusari et al. | 204/612 |
| 5,302,272 | 4/1994 | Klein | 204/603 |
| 5,312,535 | 5/1994 | Waska et al. | 204/603 |
| 5,543,026 | 8/1996 | Hoff et al. | 204/612 |
| 5,627,643 | 5/1997 | Brinbaum et al. | 204/603 X |

FOREIGN PATENT DOCUMENTS

WO 96/35810  11/1996  WIPO .

OTHER PUBLICATIONS

S. Carson et al, "DNA Sequencing by Capillary Electrophoresis: Use of a Two–Laser–Two Window Intensified Diode Array Detection" Analytical Chemistry vol. 65, No. 22 (15 Nov. 1993) 3219–3226.

Mark A. Quesuda and Shiping Zhang, "Multiple capillary DNA sequencer that uses fiber–optic illumination and detection" Electrophoresis 17 No month available (1996) 1841–1851.

Advertising Brochure on "377 DNA Sequencer" from Perkin Elmer, *Applied Biosystems Division* of Foster City, CA (1994) No month available.

Smith, et al.; "Fluorescence Detection in Automated DNA Sequence Analysis,", *Nature*, vol. 321, pp. 674–679 (Jun. 1986).

Maxam, et al., "A New Method for Sequencing DNA", *Proc. Natl. Acad. Sci.*, vol. 74, No. 2, pp. 560–564 (Feb. 1977).

Sanger, et al., "DNA Sequencing with Chain–Terminating Inhibitors", *Proc.Natl. Acad. Sci. USA*, vol. 74, No. 12, pp. 5463–5467 (Dec. 1977).

Smith, et al., "Synthesis of Oligonucleotides Containing an Aliphatic Amino Group at the 5' Terminus: Synthesis of Fluorescent DNA Primers for use in DNA Sequence Analysis", *Nucleic Acids Research*, vol. 13, No. 7, pp. 2399–2412 (1985) No month available.

Strauss, et al., "Specific–Primer–Directed DNA Sequencing", *Analytical Biochemistry*, 154, pp. 353–360 (1986) No month available.

(List continued on next page.)

*Primary Examiner*—William H. Beisner
*Assistant Examiner*—John S. Starsiak, Jr.
*Attorney, Agent, or Firm*—Fitch, Even, Tabin & Flannery

[57] ABSTRACT

An advanced imaging spectrograph system provides for slab-gel DNA sequencing and genotyping with high throughput sequencing. The system is based on the integration of improved electrophoresis structures with an imaging spectrophotometer that records the entire emission spectra along an imaging line across a sequencing gel (or capillary array). The system includes spectral shape matching to improve dye identification allowing the use of dyes having nearly any emission spectra and allowing greater than four dye multiplexing.

37 Claims, 11 Drawing Sheets

OTHER PUBLICATIONS

Connell, et al., "Automated DNA Sequence Analysis", *BioTechniques*, vol. 5, No. 4, pp. 342–348 (1987) No month available.

Wada, "Automated High–Speed DNA Sequencing", *Nature*, vol. 325, No. 26 (Feb. 1987).

Ansorge, et al., "Automated DNA Sequencing: Ultrasensitive Detection of Fluorescent Bands During Electrophoresis", *Nucleic Acids Research*, vol. 15, No. 11, pp. 4593–4602 (1987) No month available.

Wilson, et al., "Automation of Dideoxynucleotide DNA Sequencing Reactions Using a Robotic Workstation", *BioTechniques*, vol. 6, No. 8, pp. 776–787 (1988) No month available.

Landegren, et al., "DNA Diagnostics—Molecular Techniques and Automation", *Science*, vol. 242, pp. 229–237 (Oct. 1988).

Smith, "Automated DNA Sequencing and the Analysis of the Human Genome", *Genome*, vol. 31, pp. 929–937 (1989) No month available.

Mardis, et al., "Automated Methods for Single–Stranded DNA Isolation and Dideoxynucleotide DNA Sequencing Reactions on a Robotic Workstation", *BioTechniques*, vol. 7, No. 8, pp. 840–850 (1989) No month available.

Kaiser, et al., "Specific–Primer–Directed DNA Sequencing Using Automated Fluorescent Detection", *Nucleic Acid Research*, vol. 17, No. 15, pp. 6087–6103 (1989) No month available.

Carrano, et al., "A High–Resolution, Fluorescence–Based, Semi–Automated Method for DNA Fingerprinting", *Genomics*, vol. 4, pp. 129–136 (1989) No month available.

"A Strategy to Study Gene Polymorphism by Direct Sequence Analysis of Cosmic Clones and Amplified Genomic DNA", *BioTechniques*, vol. 7, No. 5, pp. 438–442 (1989) No month available.

Gyllensten, "PCR and DNA Sequencing", *BioTechniques*, vol. 7, No. 7, pp. 700–708, (1989) No month available.

Wilson, et al., "Development of an Automated Procedure for Fluorescent DNA Sequencing", *Genomics*, vol. 6, pp. 626–634 (1990) No month available.

D'Cunha, et al., "An Automated Instrument for the Performance of Enzymatic DNA Sequencing Reactions", *BioTechniques*, vol. 9, No. 1, pp. 80–90 (1990) No month available.

Edwards, et al., "Automated DNA Sequencing of the Human HPRT Locus", *Genomics*, vol. 6, pp. 593–608 (1990) No month available.

Trainor, "DNA Sequencing, Automation, and the Human Genome", *Anal. Chem.*, vol. 62, pp. 418–426 (1990) No month available.

Martin, et al., "Vision Assisted Robotics and Tape Technology in the Life–Science Laboratory: Applications to Genome Analysis", *Bio/Technology*, vol. 8, pp. 1258–1262 (1990) No month available.

Hultman, et al., "Bidirectional Solid–Phase Sequencing of In Vitro–Amplified Plasmid DNA", *BioTechniques*, vol. 10, No. 1, pp. 84–93 (1991) No month available.

Mead, et al., "Bst DNA Polymerase Permits Rapid Sequencing Analysis from Nanogram Amounts of Template", *BioTechniques*, vol. 11, No. 1, pp. 76–87 (1991) No month available.

Uber, et al., "Application of Robotics and Image Processing to Automated Colony Picking and Arraying", *BioTechniques*, vol. 11, No. 5, pp. 642–647 (1991) No month available.

Adams, et al., "Complementary DNA Sequencing: Expressed Sequence Tags and Human Genome Project", *Science*, vol. 252, pp. 1651–1656 (Jun. 1991).

Hunkapiller, et al., "Large–Scale and Automated DNA Sequence Determination", *Science*, vol. 254, pp. 59–67 (Oct. 1991).

Yager, et al., "The Human Genome Project: Creating an Infrastructure for Biology and Medicine", *TIBS*, vol. 16, pp. 454–461 (Dec. 1991).

Zuckermann, et al., "Medicinal Chemistry in a Biotech Environment: Technologies for Generating and Screening Molecular Diversity", *22nd European Peptide Symposium*, Interlaken, Switzerland, pp. 1–12 (Sep. 13–19 1992).

Marshall, "Emphasis Turns from Mapping to Large–Scale Sequencing", *Science*, vol. 268 pp. 1270–1271 (Jun. 1995).

Marshall, et al., "NIH Launches the Final Push to Sequence the Genome", *Science*, vol. 272, pp. 188–189 (Apr. 1996).

Marx, "New Methods for Expanding the Chromosomal Paint Kit", *Science*, vol. 273, p. 430 (Jul. 1996).

Schröck, et al., "Multicolor Spectral Karyotyping of Human Chromosomes", *Science*, vol. 273, pp. 494–497 (Jul. 1996).

Heller, "Engineering in Genomics: An Active Microelectronics Device for Multiplex DNA Analysis", *IEEE Engineering in Medicine and Biology*, pp. 100–104 (Mar./Apr. 1996).

AUTOMATIC SEQUENCER/GENOTYPER HAVING EXTENDED SPECTRAL RESPONSE

BACKGROUND OF THE INVENTION

The present invention relates to DNA sequencing and genotyping, and more particularly, to DNA sequencers and genotypers that use optical fluorescence detection techniques.

The basic biological characteristics of a living organism are contained in its genes or genetic code. In humans, for example, a person's biological characteristics are controlled by the genetic code contained in 23 chromosome pairs. Each chromosome contains differing genes.

The specific details of a genetic code are contained in long double helical molecules called deoxyribonucleic acid or DNA. The DNA consists of long sequence pairs of four nucleotides or bases: adenosine, cytosine, guanosine or thymidine, commonly referred to by the letters A, C, G, and T, respectively. In the double helix, the A and T nucleotides are complementary and the C and G nucleotides are complementary. Thus, the DNA molecules consist of two complementary strands that are bound together by the complements.

It is often advantageous to know the sequence of the DNA nucleotides associated with a particular gene. For example, genetic defects can be detected by analyzing an organism's genes. The DNA nucleotides for several bacteria and viruses have been sequenced, and currently, sequencing of the entire human genome is in progress. The entire human DNA consists of approximately 3 billion nucleotides or base pairs.

Existing high speed DNA sequencers use electrophoresis gel techniques, in conjunction with fractioning enzymes and fluorescent tags or markers, to separate residual DNA sequence fragments as they travel through a gel. More specifically, each DNA fragment has an incrementally different molecular weight and size. Because the mobility is related to the fragment's weight, structure, and charge, the differing fragments travel through the gel at differing speeds. Thus, the time it takes a fragment to travel through the gel relates to the fragment's mobility.

Generally, four fluorescent tags are used. These tags bind on the residual fragments in accordance with the exposed end base, if using dye terminator chemistry, or are attached to primers that are used to initiate the sequencing reaction, if using dye primer chemistry. The sequence is read by causing the fluorescent markers to fluoresce. The four fluorescent tags generally are selected to have a strong fluorescence peak that is separated from the strong fluorescence peak of the remaining tags. An optical instrument detects the emitted fluorescence signals.

Existing DNA Sequencers use an optical filter having a pass-band that is centered about the appropriate wavelength to distinguish between the dyes, and thus the fragments. The optical instrument typically includes a simple spectrometer or a filter wheel and a photomultiplier. The filter wheel has several colored filters, each filter passing light within a wavelength band corresponding to the spectral peak of one of the tags. A simple spectrograph has a wavelength-dependent light disperser such as a prism. The light disperser spreads, generally along a line, the different wavelengths of fluorescent light from the DNA fragments traveling in the gel. Four detectors are placed along the spreading line of the spectrograph at differing locations that correspond to the wavelengths associated with the fluorescent tags.

Fluorescent dyes have been found to be good fluorescent tags. Using dye primer chemistry, the tag associated with the C base often is fluorescein-5-isothiocynate (FITC) which has an emission or fluorescence peak at about 525 nanometers. The tag associated with the T base often is Texas Red, which has a fluorescence peak at about 620 nanometers. The tag associated with the G base often is Tetramethyl rhodamine isothiocynate (TRITC), which has a fluorescence peak at about 580 nanometers. Finally, the marker associated with the A base often is 4-fluoro-7nitro-benzofurazan (NBD-fluoride) which has a fluorescence peak at about 540 nanometers. Commercially, four universal primers, respectively labeled with dyes called FAM (C), TAMRA (G), JOE (A), and ROX (T), are available from Applied Biosystems, Inc. (ABI) of Foster City, Calif.

The fluorescent dyes indicated above are subject to bleaching which limits the excitation light's power level and thus the intensity of the emitted fluorescence signal from the dyes. The upper limits on fluorescence intensity limit the signal-to-noise ratio (SNR) and eventually the system's throughput.

Accordingly, there exists a need for a sequencing or genotyping system that has increased throughput and sensitivity over systems using four dyes that are distinguished by their respective fluoresce peaks. The present invention satisfies these needs.

SUMMARY OF THE INVENTION

A sequencing or genotyping system includes an imaging spectrograph that records the entire emission spectra across a plurality of lanes in an electrophoresis sequencing gel. The system includes spectral shape matching to improve dye identification, thereby allowing the use of dyes having nearly any emission spectra and allowing greater than four dye multiplexing.

In a first embodiment of the invention, the system includes a plurality of electrophoresis lanes. Each lane has a respective first and second end, and an electrophoresis medium between the first and second ends. Each lane is loaded with fluorescently-tagged charged molecules having differing mobilities and chemical properties. An electrical potential, of appropriate polarity, is applied between the first and second ends and causes charged molecules applied at the first end to travel toward the second end at a rate proportional to each molecule's mobility such that the charged molecules are separated along the lane based on the molecule's mobility. A read zone extends substantially along an image line and intersects the plurality of electrophoresis lanes near the second ends. The system also includes a light source and an imaging spectrometer. The light source illuminates the read zone with excitation light to cause the charged molecules to fluoresce and produce fluorescent light. The imaging spectrometer spectrally images the fluorescent light onto a two-dimensional imaging plane. The first dimension of the imaging plane is associated with a distance along the image line of the read zone and the second dimension is associated with the wavelength of the fluorescent light. The imaging spectrometer simultaneously images the fluorescent light onto the two-dimensional imaging plane without any scanning motions or delays.

The system-may further include a camera having a two dimensional pixel array. The camera generates video signals based on the intensity of light incident upon the pixel array. A display may display a graph of the chemical properties of the molecules crossing the imaging line verses time.

In more detailed features of the invention, the imaging spectrograph further comprises a linear entrance aperture with discrete locations along the aperture corresponding to locations along the first dimension of the image plane. Further, a plurality of optical fibers couple the fluorescent light from the read zone to corresponding locations along the entrance aperture. Alternatively, the imaging spectrograph may include an optical lens system that directly images the read zone. Further, the system may include a processor that compares the detected fluorescent light received from molecules of a given mobility with reference spectral profiles for the fluorescent tags to identify the associated fluorescent tag and thus the molecule's associated chemical property.

In other more detailed features of the invention, associated with genotyping or DNA fingerprinting, the charged molecules are at least 10 differing genetic markers of a genome and a fluorescent tag, having a unique spectral profile, is associated with each genetic marker. The processor compares the detected fluorescent light with the reference spectral profiles by calculating weighting factors, for each reference spectral profile, based on a deconvolution of the detected fluorescent light with the reference spectral profile for each of the fluorescent tags. Further, at least one fluorescent dye may be attached to charged molecules of a known mobility, to provide a mobility calibration reference. The processor calculates the mobility of any charged molecules of unknown mobility, based on the unknown molecule's travel rate and the mobility calibration reference. Additionally, the fluorescent tags used in adjacent lanes may differ from each other. The processor tracks lane drift along the image line using the difference between the fluorescent tags in adjacent lanes.

In yet other more detailed features of the invention, the charged molecules are DNA fragments and each fragment is tagged with an attached fluorescent dye that identifies the fragment's end base. The fluorescent tags are four primer dyes: FITC, TRITC, NBD-fluoride, and Texas Red, corresponding to the bases C, G, A, and T, respectively. The light source generates excitation light at wavelengths of about 488 nanometers and 514 nanometers.

The lanes are on a planar substrate and the excitation light is a laser beam that travels along the image line to simultaneously illuminate the lanes. A mirror reflects the laser beam back through the read zone along the image line to increase the intensity and uniformity of the fluorescent light. A lens couples the laser beam from a laser to the gel to increase the intensity of the excitation light traveling along the image line.

Further, optical fibers may couple the fluorescent light from the image line to an entrance slit on the imaging spectrometer. A cylindrical lens focuses the fluorescent light from the imaging line onto ends of the optical fibers and a mirror is located behind the read zone such that fluorescent light travelling away from the fiber end is reflected back toward the optical fiber ends.

In yet other more detailed features of the invention, the second dimension of the imaging plane corresponds to the spectral range from about 450 nanometers to about 900 nanometers and the wavelength within the spectral range of the second dimension so that resolution along the second dimension is less than four nanometers. Also, the excitation light is narrowband light having a wavelength within the spectral range of the second dimension so that excitation light scattered by the electrophoresis gel is imaged on a pixel array on the imaging plane. The electrical signals, generated by the pixel array based on the intensity of light collected by pixels corresponding to the wavelength of the excitation light, provide a monitor of the excitation light's intensity.

The system may further include first and second electrodes for applying the electrical potential to the lanes at the first and second ends, respectively. The first and second electrodes extend across all of the plurality of lanes. Also, a plurality of loading electrodes may be situated in each lane near the first electrode for loading the charged molecules into the lanes.

The electrophoresis medium may be a gel having a thickness of 200 microns which is sandwiched between two glass plates. An index matching buffer may optically couple the light from the light source to electrophoresis medium. The read zone may further include fluorescent markers at each end of the image line for indicating the read zone. Also, the plurality of electrophoresis lanes may include 384 separate parallel lanes. A heater may be thermally coupled to the electrophoresis medium for maintaining the medium within a predetermined temperature range.

The present invention is further embodied in a method for sequencing DNA. First, DNA fragments that are tagged with fluorescent dyes are produced. The dyes indicate an end base associated with the respective DNA fragment. Next, the DNA fragments are separated according to mobility using electrophoresis of the fragments on a plurality of electrophoresis lanes. The separated DNA fragments form fragment groups of slightly different mobility. Next, the fragment groups are excited with excitation light causing the fluorescent tags to fluoresce. Next, a hyperspectral image is formed of the separated DNA fragments. The hyperspectral image simultaneously covers all of the electrophoresis lanes and a broad spectral range. Next, the fluorescent dye associated with DNA fragments of particular molecular weight is identified by fitting the spectra emitted by a fragment group with reference spectra associated with the fluorescent dyes.

In another method of identifying molecules tagged with fluorescent dyes, in accordance with the present invention, a hyperspectral profile is formed of a molecules' fluorescence emission. The hyperspectral profile covers a wavelength range from 450 nanometers to 900 nanometers with a resolution of less than 5 nanometers. Next, the hyperspectral profile is convoluted with a reference spectral profile of each dye over the entire spectral range to generate a weighting factor for each dye. Finally, the contribution of a particular dye to the molecules' fluorescence emission is indicated based on the weighting factor.

The present invention is additionally embodied in a method for loading charged molecules of differing mobilities into a plurality of closely spaced electrophoresis lanes. Each lane has first electrophoresis electrodes located at a first end of the lane, second electrophoresis electrodes located at a second end of the lane, and a loading electrode located near the lane's first end. First, a solution having the charged molecules is applied over the loading electrode of the first lane. Next, a first voltage is applied to the first and second electrophoresis electrodes of the first lane. The first voltage has the same polarity as the charged molecules. The charged molecules are then loaded into the first lane by applying a large second voltage, having a polarity opposite the polarity of the charged molecules, to the loading electrode of the first lane. A third voltage is applied to the loading electrode of previously loaded lanes while the loading process is repeated for the remaining electrophoresis lanes. The third voltage is a reduced value of the first voltage. After loading the lanes, a fourth voltage is applied between the first electrophoresis electrode and the second electrophoresis electrode to cause the charged molecules to migrate through the electrophoresis lane at a rate proportional to the molecules mobility.

In this method, the charged molecules are negatively charged DNA fragments. Further, the first voltage is between about −1 and −2 volts, the second voltage is between about +1 and +2 volts, the third voltage is between about −0.1 and −0.2 volts, and the fourth voltage is between about −2000 and −4000 volts.

Finally, the present invention is further embodied in a method of identifying fluorescently-tagged DNA base fragment groups. First, the fragment groups are excited with excitation light to cause a fluorescent tag associated with a respective fragment group to fluoresce and produce fluorescent light. Next, the fluorescent light emitted by each fragment group is detected over a sufficiently large wavelength range to produce a spectral profile of the fluorescent light from each fragment group. Next, the detected spectral profile from each fragment group is compared with reference spectral profiles associated with the fluorescent tags to generate a weighting factor. Finally, the fluorescent tags associated with each fragment group are identified based on the fragment group's weighting factor. In a more detailed feature of the method, the wavelength range extends from about 450 nanometers to about 900 nanometers.

BRIEF DESCRIPTION OF THE DRAWINGS

The above and other aspects, features and advantages of the present invention will be more apparent from the following more particular description thereof, presented in conjunction with the following drawings, wherein.

Corresponding reference characters indicate corresponding components throughout the several views of the drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
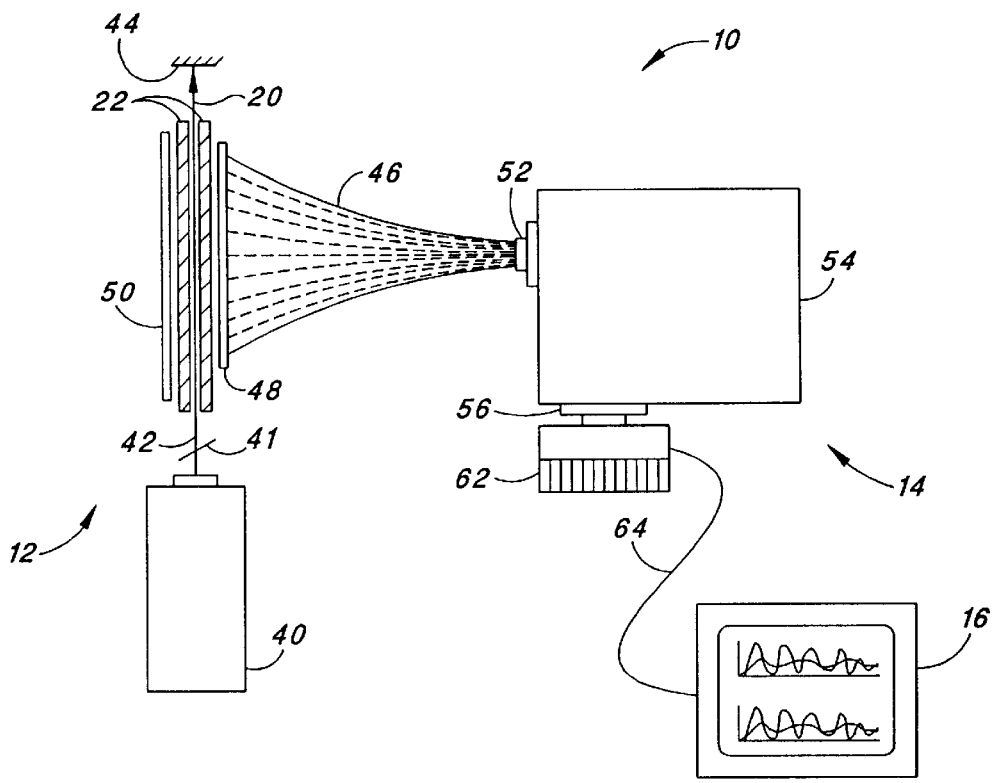
FIG. 1 is a block diagram of the imaging spectrograph sequencer/genotyper embodying the present invention.
Figure 5:
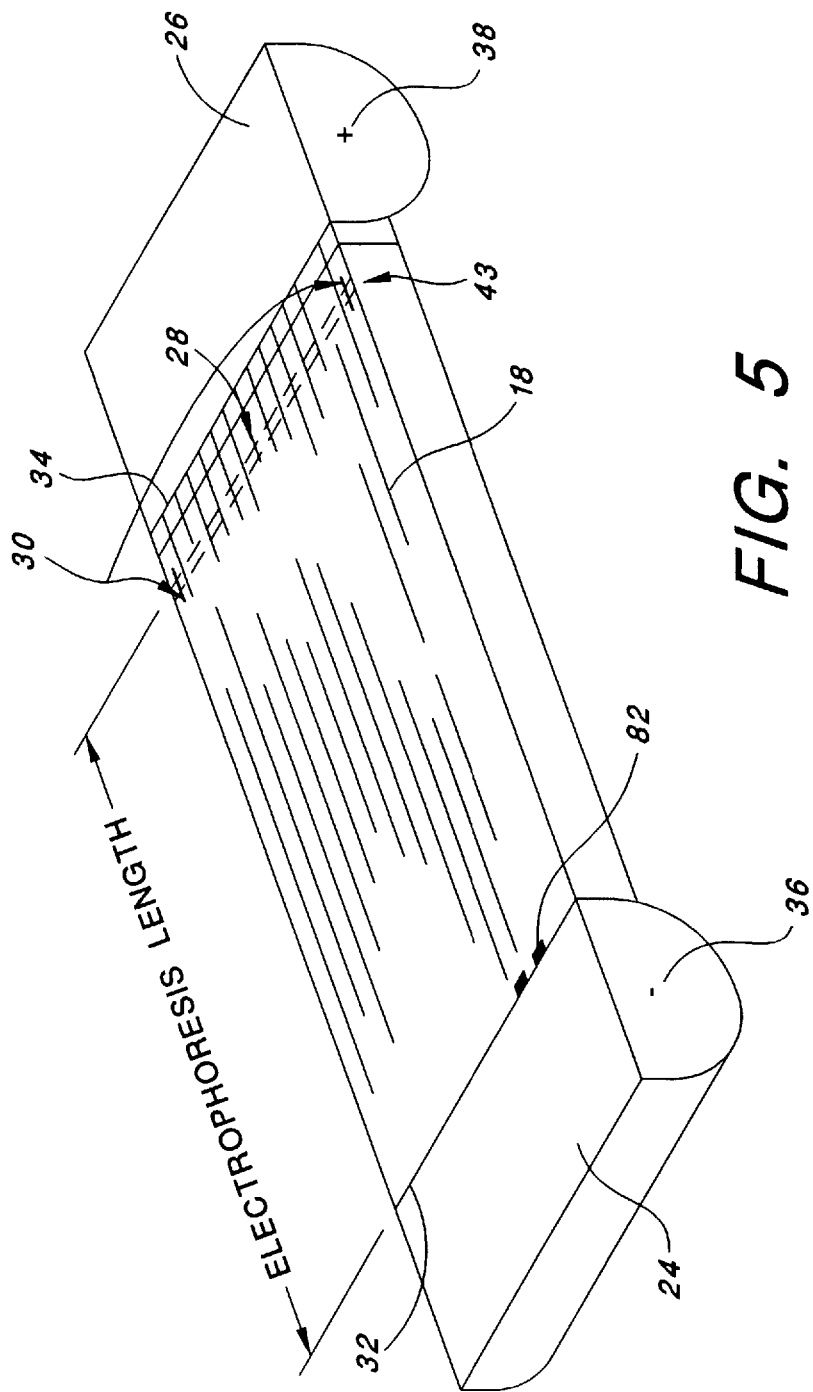
FIG. 5 is a perspective view of electrophoresis lanes in an electrophoresis gel, in accordance with the present invention, having electrostatic loading pads.
Figure 6:
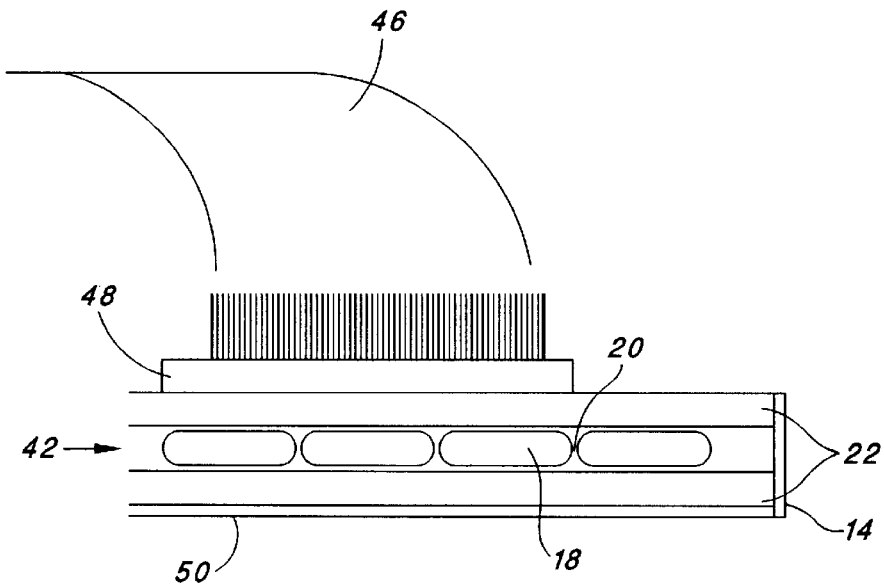
FIG. 6 is a cross-section of the electrophoresis lanes of the apparatus of FIG. 1, showing the orientation of the electrophoresis lanes, excitation light, detection optical fibers, and reflective mirrors, in accordance with the present invention.

As shown in exemplary drawings, and particularly in FIGS. 1, 5 and 6, the present invention is embodied in a sequencing or genotyping system 10 that records the entire emission spectra of fluorescent dyes attached to nucleoprotein fragments. The entire spectra is then compared against reference spectra, corresponding to the fluorescent dyes, to identify the particular fluorescent dye associated with a fragment group.

The system 10 includes an electrophoresis device 12, an optical imaging device 14, and a processor 16. The electrophoresis device (FIGS. 1 and 5) includes 384 lanes 18 formed in an electrophoresis gel 20. The electrophoresis gel 20 has a thickness of 200 microns and is sandwiched between two flat rectangular glass plates 22. The glass plates have a width of about 25 centimeters (cm) and a length of about 60 cm. The lanes 18, having a total width of about 23 cm, run parallel with the length of the glass plates 22 between a first or loading buffer chamber 24 and a second or collection buffer chamber 26. A read zone 28 is located across the lanes near the second buffer chamber. Synthetic gems, such as ruby, placed at each end of the read zone, can act as fluorescent alignment markers 30 of the read zone.

The fluorescently tagged nucleoproteins are placed in the first buffer chamber and introduced at a first end 32 of the lanes. A second buffer chamber at the second end 34 of the lanes receives the nucleoproteins after they have passed through the lanes. A negative electrode 36 is coupled to the first buffer chamber 24 and a positive electrode 38 is coupled the second buffer chamber 26. A high voltage potential of e.g., 2000 volts, is applied between the negative electrode and the positive electrode causing the negatively charged nucleoproteins to travel through the electrophoresis gel 20.

A power supply (not shown), having a voltage range up to 4000 volts at up to 200 milliamps, supplies the high voltage potential. The electrophoresis gel 20 is typically acrylamide and the nucleoproteins travel through the gel at a rate proportional to the nucleoprotein's molecular weight or mobility. More particularly slightly lighter and smaller nucleoproteins, have a higher mobility and travel through the gel faster than longer nucleoproteins, thereby arriving at the read zone 28 sooner.

In DNA sequencing, the individual nucleoproteins are DNA residual fragments having differing molecular weights and mobilities based on the location of the nucleotide or base at which the DNA molecule was fragmented. The exposed base of the DNA fragment is coupled to a fluorescent dye that tags the fragment in accordance with the exposed base. Accordingly, as the fragments of differing mobilities pass by the read zone 28 and are "read" as "identified" as taught herein, they may be used to identify the sequence of the original DNA molecule.

In genotyping, DNA fragments (markers), exhibiting a distribution of sizes and lengths forming a unique signature for the DNA sample, are analyzed. These distributions, with each individual marker tagged, can be multiplexed and read out in each lane in a genotyping operational mode.

An argon ion laser 40 illuminates the read zone 28 with excitation light 42 directed from the side of the electrophoresis gel 20 causing all the lanes 18 to be simultaneously illuminated by the laser's excitation light. A lens 41 placed between the laser 40 and the edge of the electrophoresis gel 20 improves the excitation light 42 coupling into the gel. Further, the plates 22 act as a light guide by internally reflecting the excitation light. A matching solution or buffer 43 may be used between the air and the gel to lower reflections caused by the air-gel interface. A laser beam reflecting mirror 44 (FIG. 6), located opposite the laser 40, reflects the excitation light 42 passing through the read zone so that the excitation light 42 makes a second pass through the same region to increase the intensity and uniformity of the read zone illumination. The excitation light 42 from the argon ion laser has two principle wavelengths at approximately 488 nanometers and 514 nanometers. These wavelengths are advantageous for causing a wide variety of fluorescent dyes to fluoresce. Additional or other lasers that provide excitation light 42 having a wavelength matching the excitation spectra of the dyes may be used.

The fluorescent light emitted by the dyes is captured by and is focused onto a liner fiber-optic array 46 by a cylindrical lens 48 or by a micro-lens assembly. A flat or cylindrically concave mirror 50, disposed opposite the optical fiber ends, reflects fluorescent light back through the gel toward the optical fibers 48. The fluoresce signal is coupled through the optical fibers to an entrance slit 52 of an imaging spectrograph 54 (FIG. 1). The entrance slit 52 is filled with an elongated line of optical fiber ends. The light passing through the slit 52 is wavelength resolved by the imaging spectrograph 54 in an astigmatic manner, thereby producing a two-dimensional image at an image plane 56.

Figure 7:
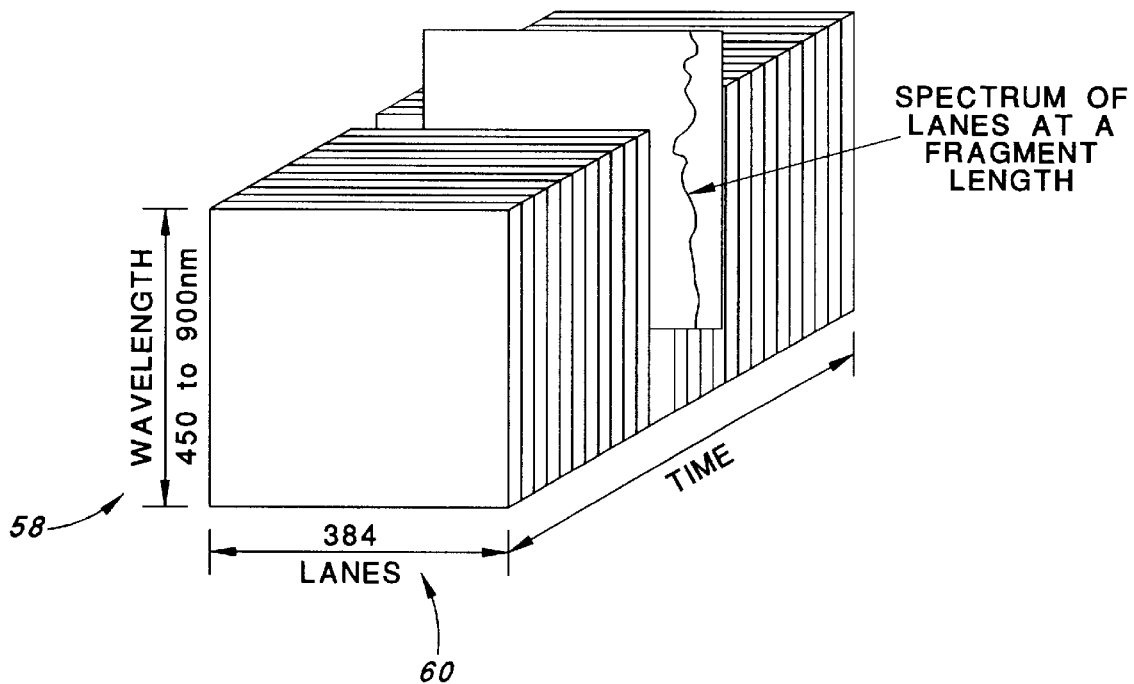
FIG. 7 is a perspective view of the successive frames, forming an image cube, indicating the relationship between the lanes, the wavelengths, and the time or mobilities.

As shown in FIG. 7, the first dimension 58 of the image, as discussed in more detail below, is related to the wavelength of light at the slit 52. The second dimension 60 is related to the distance along the entrance slit 52 at which the incoming light passes through the slit and corresponds to distances along the read zone 28 which crosses the lanes 18. Accordingly, the imaging spectrograph produces a simultaneous spectral image of all the electrophoresis lanes 18 at its image plane 56.

A cooled CCD camera 62 is oriented in the image plane 56 and detects the two-dimensional image. A suitable camera would be the Photometrics model Sensys 1600 of Tucson, Ariz., or the Scientific Imaging Technologies model S1424A. The camera converts the two-dimensional image into a digital video signal which is transmitted across a data link 64 to a data acquisition computer 16.

The CCD camera 62 has a resolution of about 1500 pixels across the spatial dimension 60 of the lanes 18. Thus, each of the 384 lanes is imaged onto about 4 pixels. Preferably, the pixels are binned together in either the spacial or spectral dimension, or both, during readout to lower the number of bytes in the digital video signal. Thus, the imaging spectrograph 54 and camera 62 create a hyperspectral image of the lanes.

A hyperspectral imager (HSI) 14 is distinguished from a multi-color spectrometer system which typically has several discrete spectral channels with broad-band properties (i.e., several tens of nanometers in bandwidth). A typical hyperspectral imager has continuous channels less than 5 nanometers wide. In the spectral dimension, the hyperspectral imager has a spectral resolution of about 3–4 nanometers, contiguously spaced between about 450 nanometers and 900 nanometers. Because the imaging spectrograph 54 provides a hyperspectral image for wavelengths between about 450 and 900 nanometers, more of the emitted fluoresce signal is collected and used in identifying the fluorescent dyes. This is particularly valuable since the emission spectra of the dyes overlap.

Figure 2:
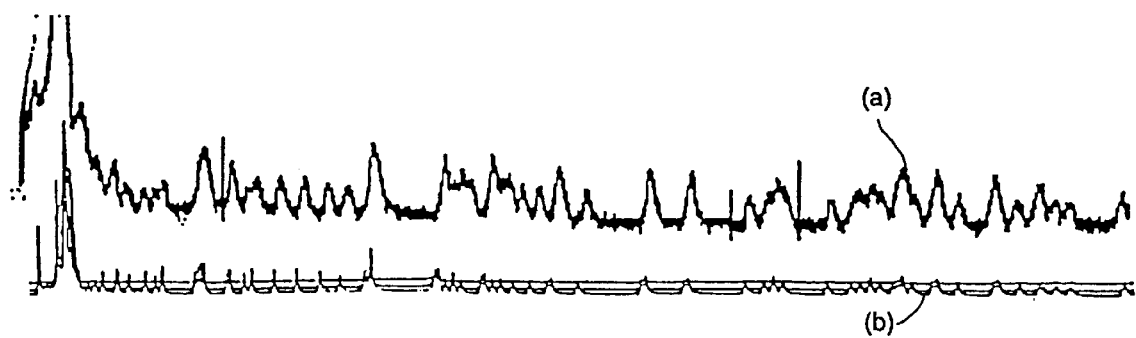
FIG. 2 is a graph comparing the output intensity as a function of time for one fluorescent dye attached to DNA molecules moving past the detection system of the imaging sequencer/genotype of the present invention, with the output intensity of an existing system.

FIG. 2 compares, at one wavelength, the signal (trace b) received from one dye in a lane of an existing system, and the signal (trace a) for the fluoresce dye received from a lane by the system of the present invention. The genetic sequence is of the bacteriophage M13mp18 taken with a monochrometer set at the wavelength of 520 nm, which corresponds to the fluorescence of the dye associated with the base cytosine (C). The other three bases are not marked with a dye. The sample size used in both traces is the same. Using the entire spectral content would result in even a higher signal for the system of the present invention.

Figure 3A:
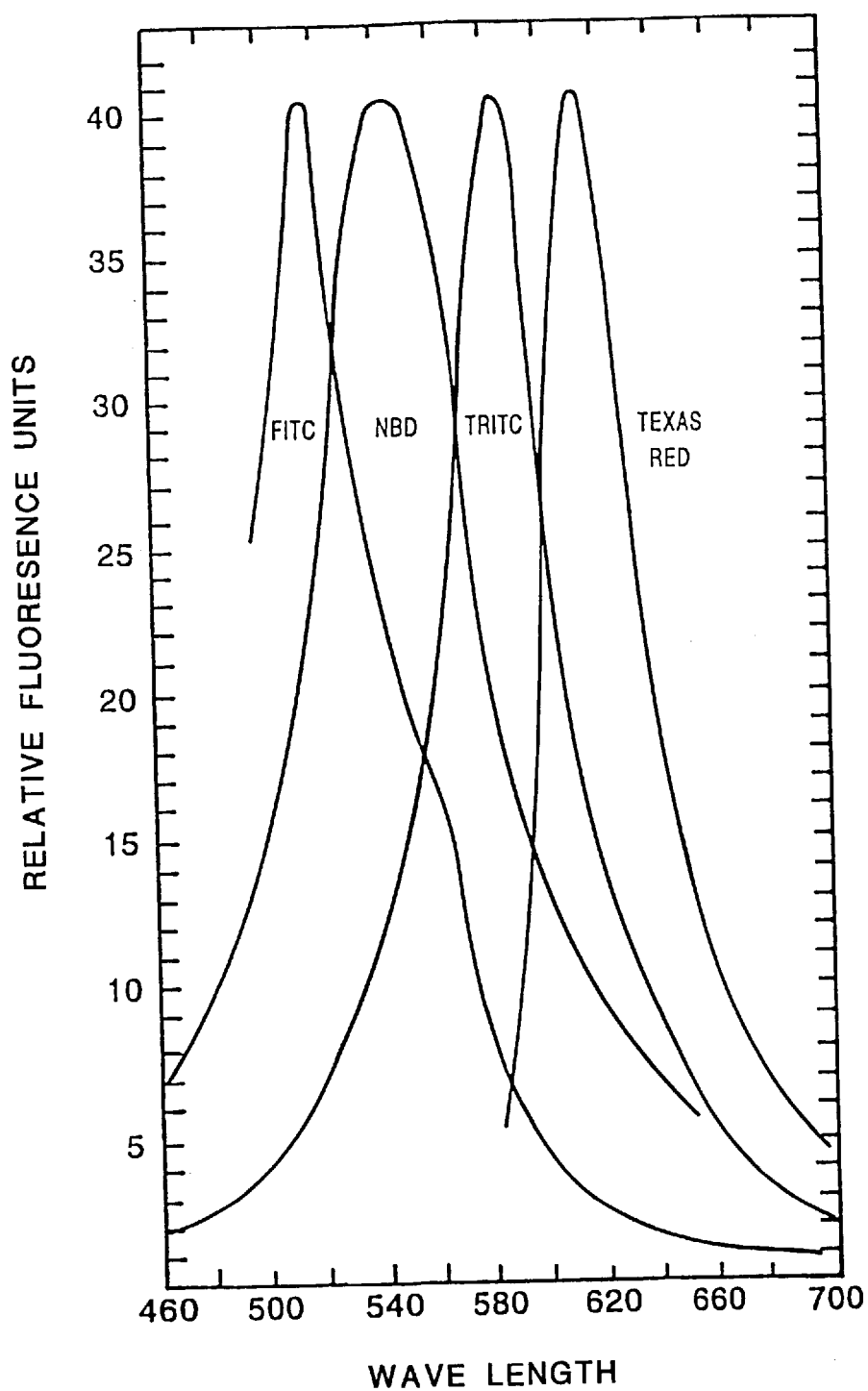
FIG. 3A is a graph of the emission spectra of four common fluorophores used as tags in existing systems.
Figure 3B:
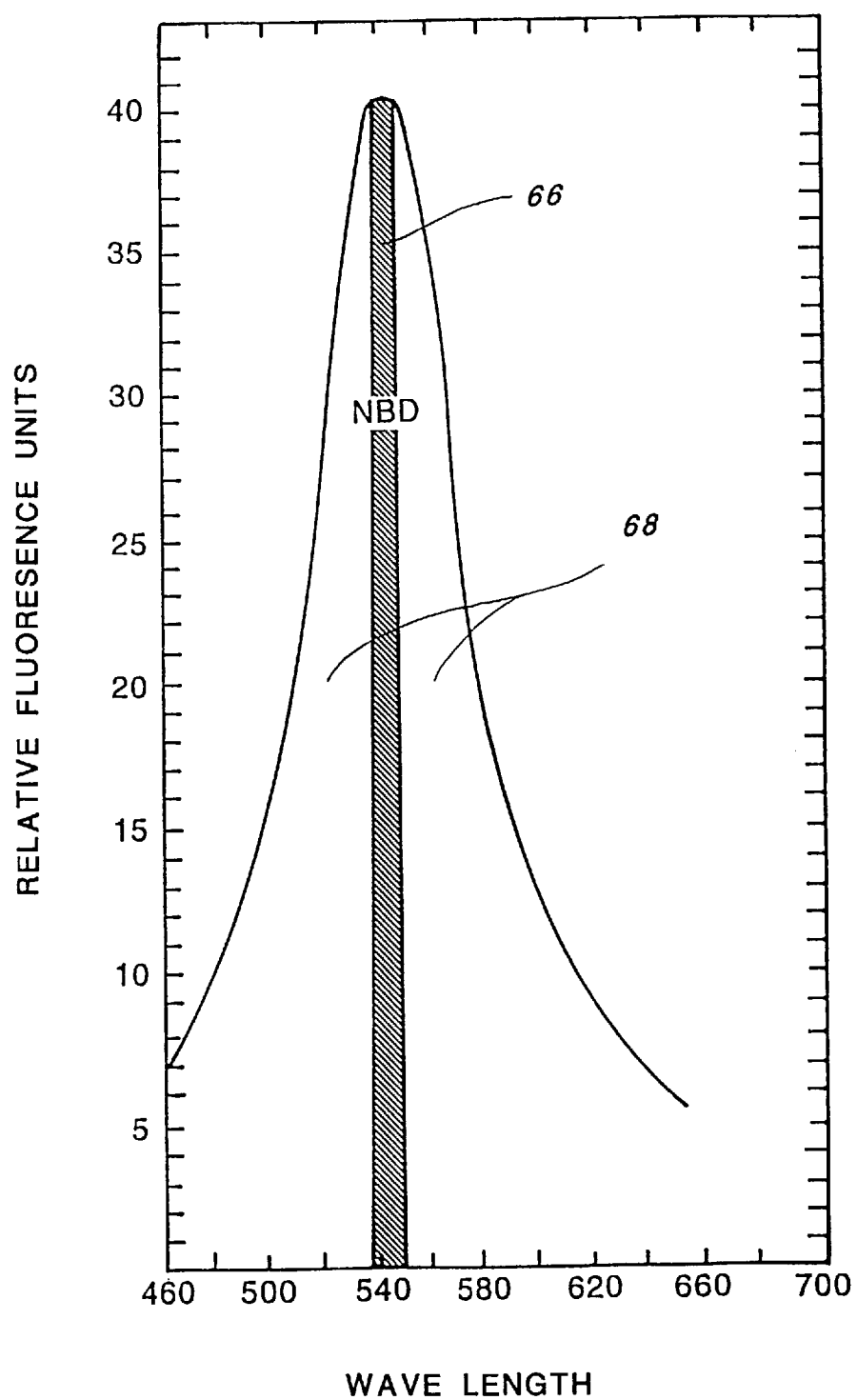
FIG. 3B is a graph of the emission spectra of the fluorophore NBD, indicating the additional light intensity that fails to be collected by a passband filter of the prior art and that is collected by the imaging spectrograph sequencer of the present invention.

More particularly, as shown in FIGS. 3A and 3B, the spectral signal of common dyes encompass a very wide spectral band. Existing systems, however, merely look at a narrow window 66 (FIG. 3B) centered about the peak of a dye's fluoresce spectra to identify the particular fluoresce dye. Accordingly, the fluoresce signal falling in the spectra 68 outside the narrow window is ignored by existing systems and the energy within the envelope of the profile of the fluoresce signal is lost and not used.

As discussed in more detail below, the processor 16 of the present invention compares the spectral profile of the received fluoresce signal with a reference profile for each of the dyes in use. A weighting factor between the spectral shape of the received signal and the reference spectra results in a more accurate determination of the dye associated with the fragment.

Figure 4:
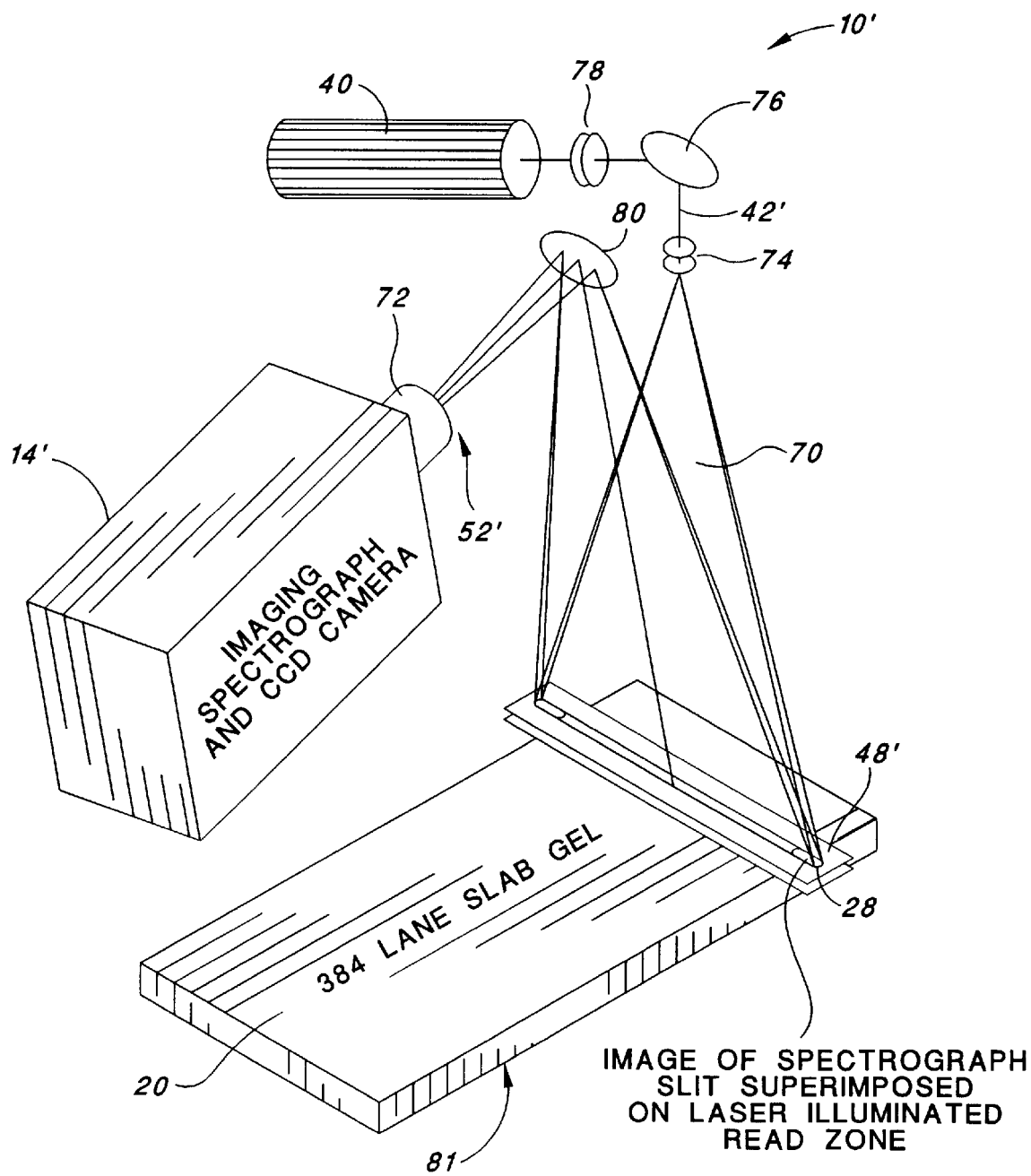
FIG. 4 is a perspective view of another embodiment of the imaging portion of an imaging spectrograph sequencer of the present invention.

An alternative embodiment of the optical system 10' is shown in FIG. 4. In this embodiment, the excitation light 42' from the argon ion laser 40 is spread by an aspheric cylindrical lens set 74 into a beam fan 70 that simultaneously illuminates the read zone 28. A first turning mirror 76 and an electro-optical shutter 78 assist in controlling and directing the excitation light. A camera of the imaging device 14' has optics 72 that directly image the linear read zone 28, through a second turning mirror 80 and a slit 52', and spectrally disburses the fluoresce light to similarly produce a two-dimensional image. No fiber-optic bundle is used in this embodiment because the read zone 28 is directly imaged onto the image plane. A cylindrical lens 48' may be used just over the read zone 28. A thermal jacket or heater 81 may be coupled to the electrophoresis gel support to stabilize the gel temperature and thus, the lane uniformity. Like the previous embodiment, one dimension 58 of the two-dimensional image corresponds to a distance along the read zone 28, and the other dimension 60 corresponds to the wavelength range between about 450 and 900 nanometers.

Referring again to FIG. 5, each lane 18 has an electrostatic loading pad 82. The loading pads 82 can have a dimension as small as 10 microns square. A sample is concentrated onto the pad 82 by placing a small sample onto or near the pad 82 and applying a negative voltage potential, about 1 volt, to the pad 82 that attracts the negatively charged fragments to the pad 82. After the charged fragments are loaded in the lane, a small voltage potential, on the order of 0.1 to 0.2 volts, is applied to the loading pad 82 while the loading process is repeated for the remaining lanes 18. The voltage potential at the electrostatic loading pad 82 is then removed, and a positive 1 volt potential is applied, causing the charged molecules to leave the pad and enter the lane 18. The fragments are then run down along the lanes by applying a large negative voltage potential between the negative electrode 36 and the positive electrode 38. A sample as small as 14 picoliters can be placed in a lane 18 by pipetting the DNA sample onto or near a loading pad 82 and performing the loading process.

Alternatively, a mechanical gel loading system (not shown) can precisely pipette samples to a gel 'comb' region of the gel. The gel comb can be either a traditional comb or the electrostatic loading pads or concentrators discussed above. The mechanical system can be coupled to the sequencing/genotyping system 10 using a nulogic 3-axis controller and a National Instruments I/O system that can control pipetting and access alignment electronics having IR sensors. Such a system can be mounted above the gel 20, in a region arranged to be near ground potential, and can transfer liquids from a chilled microwell plate (to minimize evaporation losses). The picopipettor can utilize teflon microtube fibers reinforced with ceramic insulators. When used in conjunction with electrostatic loading pads 82 discussed above, the samples can be synchronized if necessary. If alternating lanes 18 loaded and started, and then the remaining lanes are loaded and started, finding the lanes is easier for the processor 16. The electrostatic loading pads 82 can gather charged DNA from the loading volume and hold it in the vicinity of a coated metalized or other conducting electrode (preferably indium tin oxide, gold, or platinum).

The electrostatic loading may be performed on or off the sequencer 10. If the loading is performed off the sequencer 10, then in the electrophoresis device 12 may be transported with the samples attached, installed in the sequencer, and the samples released. In either case, the very small pads may be loaded from a much larger volume (microliters), and the samples may be concentrated and spacially located, thus narrowing the lanes and allowing more samples to be loaded across a given gel width. Electrostatic loading reduces the precision required to spacially place a sample volume in the lane, because precision is gained by the concentration of the sample at the pad 82. Accordingly, the sequencer/genotyper 10 of the present invention can sequence with DNA samples as small as 140 nanograms or with cosmid samples as small as 12 nanograms.

With reference to FIG. 7, it is seen the imaging spectrograph produces a series of frames as a function of the fragment length. Each frame has one dimension corresponding to the 384 electrophoresis lanes, and another dimension corresponding to the wavelength spectra, between about 450 to 900 nanometers. The timing between frames is set to gather fluorescent light from the fragment groups as they pass through the read zone. A frame rate of 1 to 2 frames per second is sufficiently rapid to image the fragments as they pass through the read zone. If the fluorescent light from a particular fragment group is included in a more than one frame, then the signal for that fragment group from successive frames can be summed together.

Figure 8A:
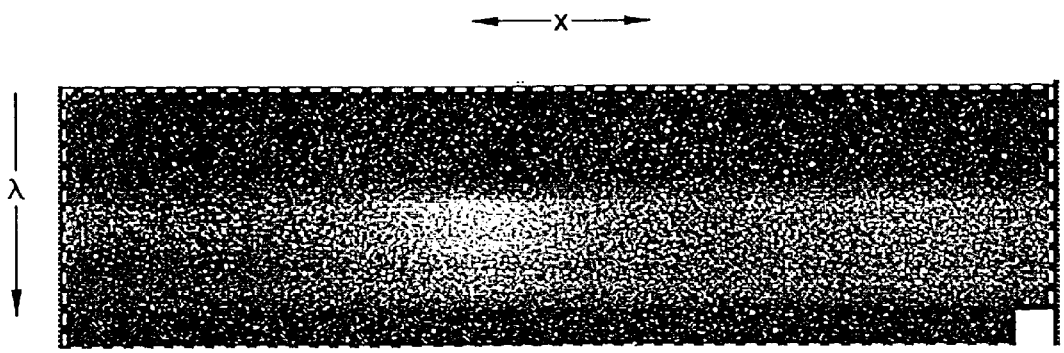
FIG. 8A is an image of a lane trace showing raw data obtained using the imaging spectrograph of FIG. 1.
Figure 8B:
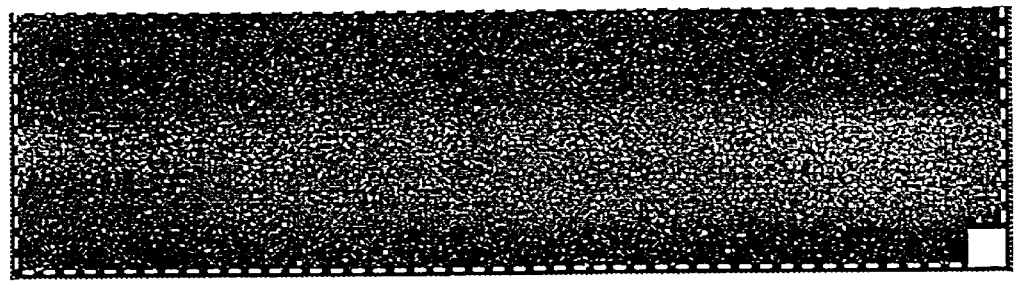
FIG. 8B is an image of a line trace showing background data corresponding to the imaging spectrograph and the electrophoresis gel of FIG. 1.
Figure 8C:
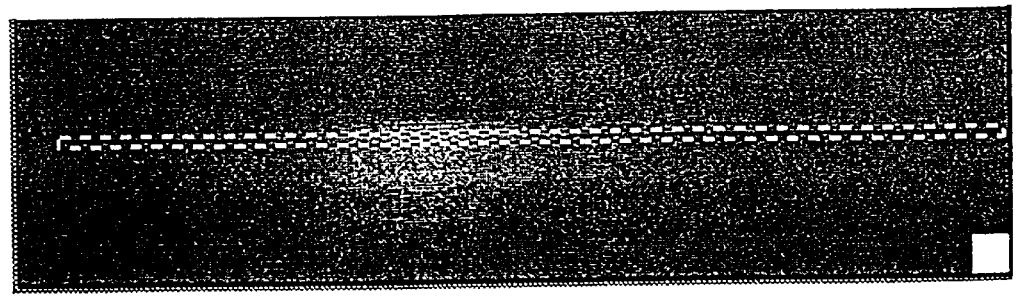
FIG. 8C is an image of an lane trace showing the net result of the combination of the image of FIG. 8A minus the image of FIG. 8B, yielding the emitted fluorescence signal from the lane trace.

As shown in FIG. 8A–8C, the processor 16 removes background information by taking a signal from the lanes 18 and subtracting a background scan to produce an enhanced scan. FIG. 8A is an image of a "raw" data frame that includes the fluorescent light from a lane along with "background noise." The fluorescent light is produced by dyes associated with dye primer chemistry, discussed above. FIG. 8B is an image of the lane before the fluorescent dyes enter the read zone, indicating the background noise. The fixed pattern of the background noise in the CCD camera 62 is determined from field flats and the dark current from dark frames (FIG. 8B). The background noise is processed out of the raw data (FIG. 8A) so that only the dye's spectral signature remains (FIG. 8C). However, noise components produced in the statistical "Poisson" detection process cannot be eliminated.

Figure 9A:
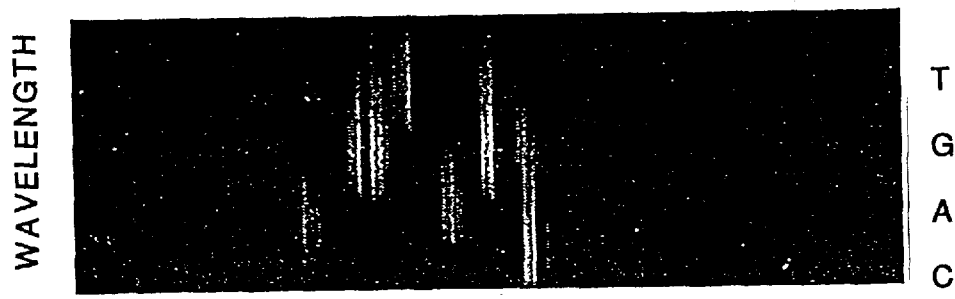
FIG. 9A is a single image from the image cube of FIG. 7, showing the fluorescence signal received from six lanes having differing dye tags and the corresponding emission spectra of the tagged DNA.
Figure 9B:
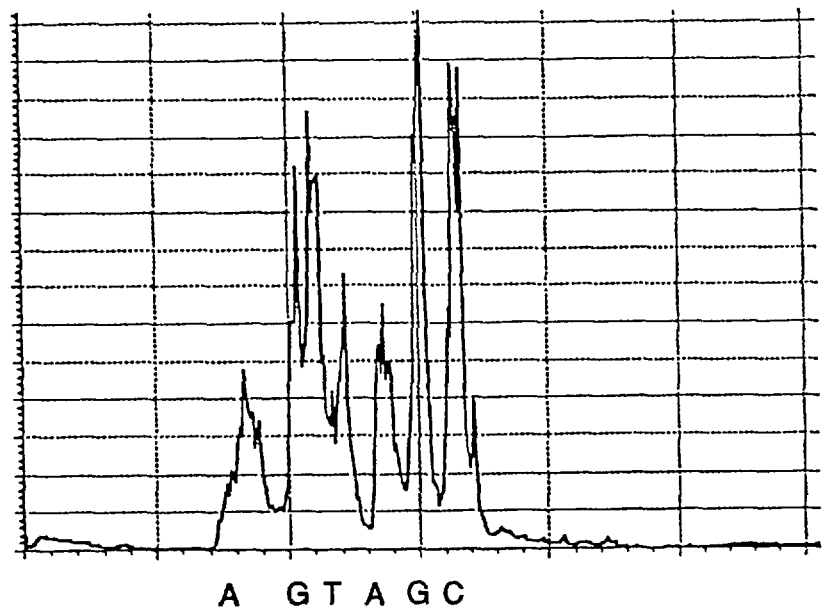
FIG. 9B is a graph for the integrated wavelength values, over a spectral range of FIG. 9A, verses lane.

As shown in FIGS. 9A, the imaging spectrograph 10 of the present invention produces an image of the entire emission spectra of a fluorescent dye. The emitted fluorescent light is produced by dyes associated with dye primer chemistry. As discussed in more detail below, the processor correlates the measured spectra with reference spectral profiles, and based on the correspondence of all the dye's fluoresced light, calculates a weighting factor. Based on the weighting factor, the processor is able to identify the particular fluoresce dyes, and then identify the corresponding base. In FIG. 9B, the graph shows the integrated light intensity falling in the spectra ranges corresponding the dyes of the indicated bases.

Figure 10:
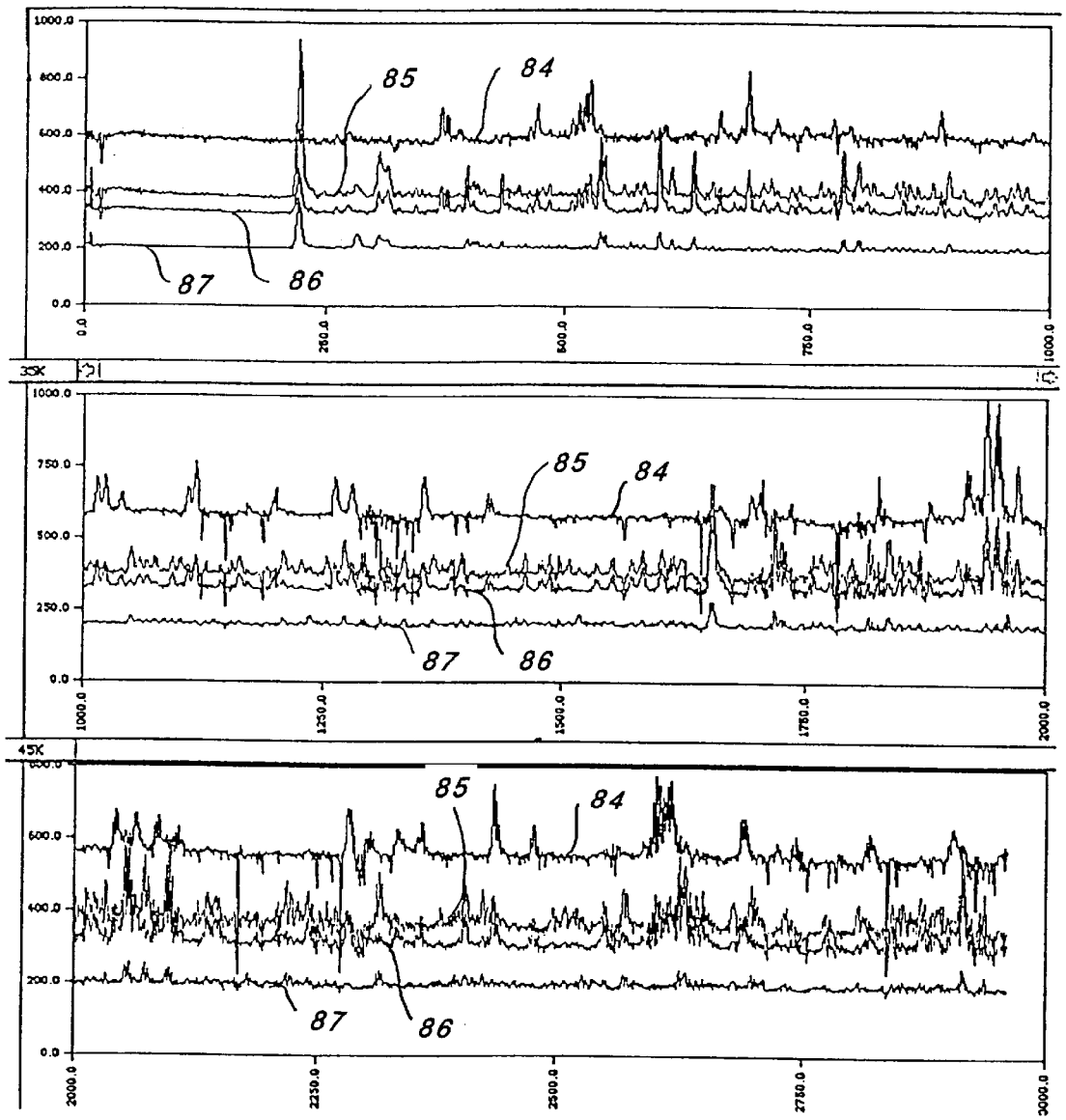
FIG. 10 is a graph showing the time-dependant emission of four dyes attached to DNA, as detected by the imaging spectrograph.

As shown in FIG. 10, the time dependent emission of the four dyes is shown in four traces. A trace file consists of data for the four traces. These dyes are associated with dye terminator chemistry and are also available from ABI. Each trace represents a wavelength band corresponding to the respective dyes. The trace baselines are shifted to separate the curves for improved viewing. The top curve 84 is produced by the FAM dye terminator and is associated with the G base. The next curve 85 is produced by the TAMARA terminator dye and is associated with the T base. The next curve 86 is produced by the R6G terminator dye and is associated with the A base. The bottom curve 87 is produced by the ROX dye and is associated with the C base. The processing system 16, because it has the entire spectral information, is able to resolve the presence of any or all of the dyes passing the read zone 28 in any given lane 18 even if the dyes arrive at the read zone simultaneously. Accordingly, the present invention allows the use of multiple dyes, or dye multiplexing, to enhance the performance of the sequencer or genotyper 10. From this "trace" information the base letters can be assigned or called using the image processing software. By comparing each dye emission in the four traces by size, peak width, peak position, relative to other peaks, the sequence of letters is determined.

An important feature of the invention is that new dyes may be used for multi-color tagging of base pairs, using six to eight, or more, fluorophores. This is particularly of value for fragments marked for genotyping (DNA finger printing) where many fragments need to be measured simultaneously. The spectra of each specific fluorophore is stored in the image processing software. These known spectra permit spectral unmixing of detected multiple fluorophones, and by use of correlation (deconvolution) techniques, utilize the full energy in each dye spectra to enhance the base-calling detection and accuracy. The ability to more accurately resolve dyes with similar emission signatures (i.e. close peak wavelenths) using the entire emission spectra deconvolution expands the number of possible dyes used in a single run beyond those in current use. In particular, a new set of SYBR dimeric cyanine or Bodipy dyes, commercially available from Molecular Probes, Inc. of Eugene, Oreg. are excitable with the 488 nm argon ion laser line, have potential as candidates for multiplexing and sequencing dye sets. The commercially available dye set has 8 members with peak emission wavelengths that span from about 460 to about 670 nanometers, within the identification range for the imaging spectrograph.

Further, by using eight fluorescent dyes, the dyes can be alternated so that adjacent lanes do not use the same dyes. Alternatively, a fifth dye can be added to every second lane for use in lane tracking.

Additionally, dyes that produce infrared emission light having a wavelength including 1300 nm may be used. These dyes would be excited with, for example, infrared diode lasers. Also, the spectral range of the imaging spectrograph would be shifted or extended to be responsive to the infrared emission light.

Figure 11:
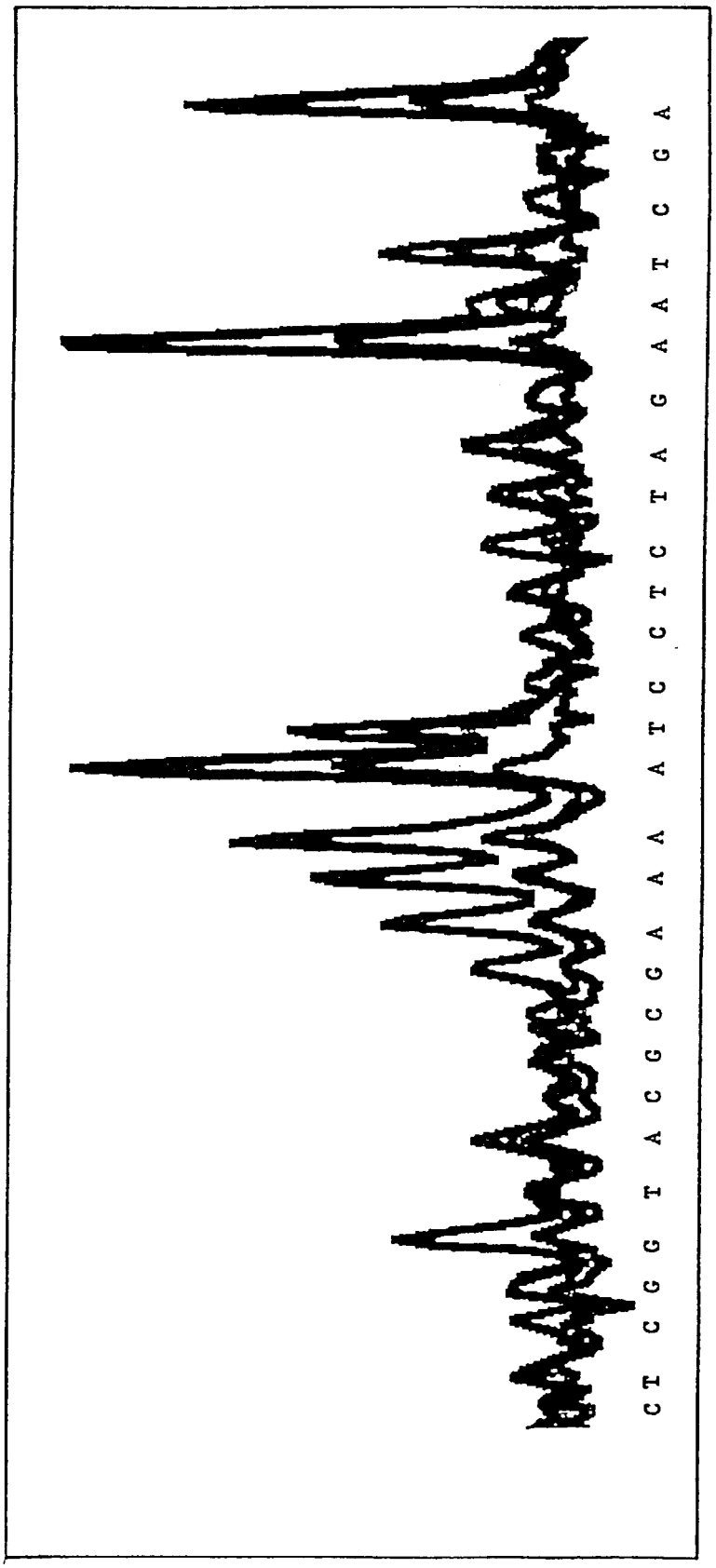
FIG. 11 is a graph showing the time-dependent emission of four dyes, attached to DNA and the corresponding bases derived from the four peaks.

FIG. 11 shows a time-trace of the fluorescence emission spectra for the four dyes. The traces are based on the intensity of light within the several pixels corresponding to the wavelengths associated with each base's dye. The baseline for each trace is arbitrarily shifted to better view the curve for each base. By comparing the magnitudes of the traces it is possible to identify or call the sequence of the DNA sample by determining the dye moving past the optics.

Figure 12:
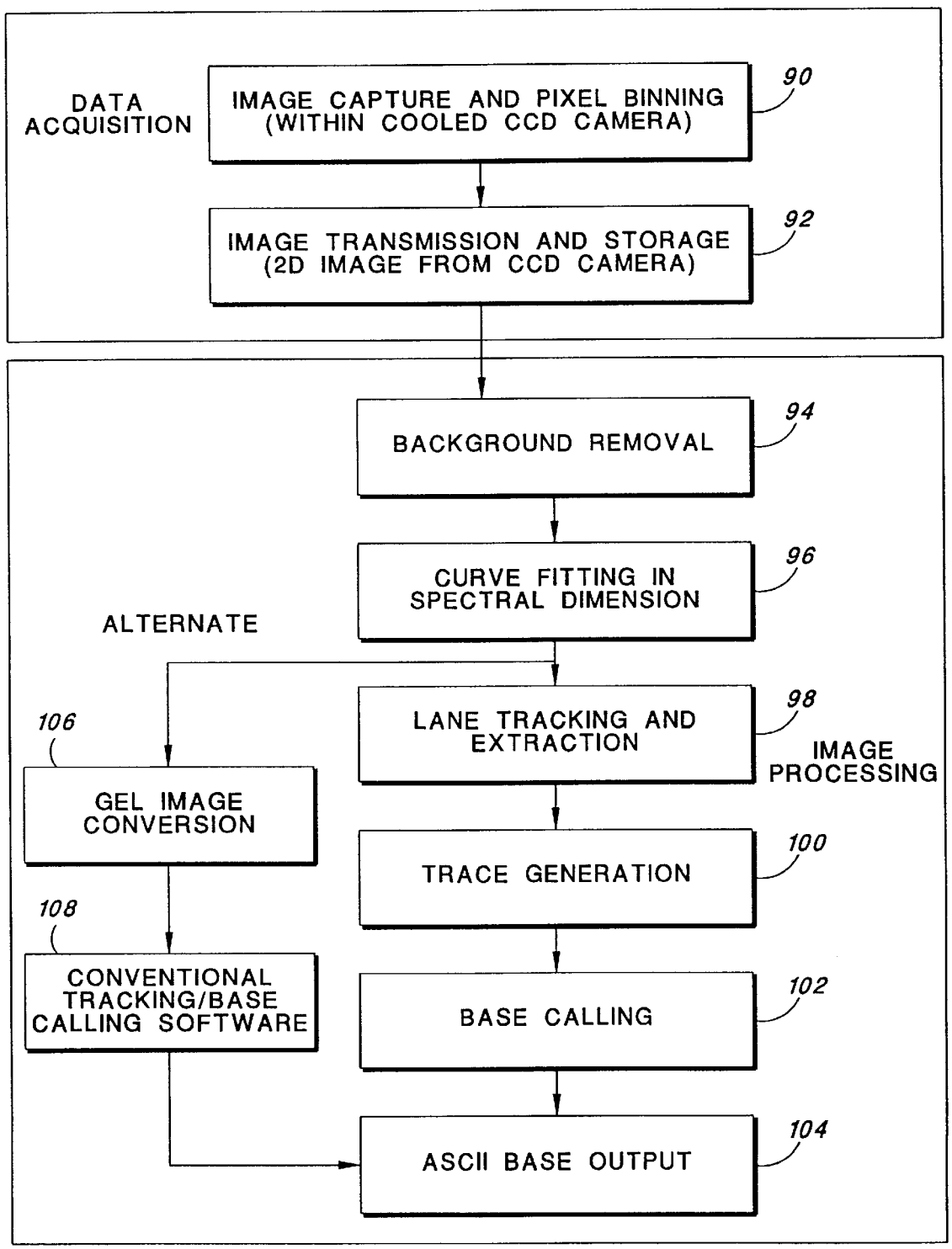
FIG. 12 is a flow diagram of the data acquisition and image processing methods of the present invention.

The spectral profile matching and data analysis is performed using a process shown in the flow diagram of FIG. 12. In the first step 90, the image that is captured in adjacent pixels are binned together. The CCD data acquisition software continuously downloads data from a CCD camera onboard buffer to the computer memory. The camera acquires from 1 to 2 frames a second. Each frame consists of 524,288 numerical values using a 12-bit pixel resolution. The data may be transmitted via a SCSI port or a PCI bus directly to the computer's disk.

In the next step 92, the data from the CCD is sent to the processor 16 where, in the next step 94, the background data is removed. In the next step 96, spectral matching with the stored library of fluorophore spectra (signature) is performed in order to generate 'trace' data (or files). The spectral matching to the first fluorophore is performed and then that information is amplitude subtracted from the raw data. The residual data is then matched to the signature of the second fluorophore, noted, subtracted until all the fluorophore spectra have been removed and the residual is minimized. The simple linear mixing/un-mixing produces an equivalent of the standard four color trace file, but it represents a more advantageous method by operating on significantly more spectral data (instead of just the output from a set of 4 filters or spectral windows). The method of the present invention yields significantly more sensitivity. The spectral unmixing detection algorithm, to determine the mix of fluorophores in a pixel, is advantageous to remove 'spill-over' or leakage of signal from one channel to another, which is typical on current machines especially since the broad emission spectra of the dyes overlap.

In the next step, 98, each lane is tracked and extracted from the image. Because of transverse mobility nonuniformities, the lanes (migrating samples) slowly move horizontally or laterally in time. Each lane must therefore be followed or "tracked" across the image plane. Each tracked lane is extracted from the rest to give a "trace" that represents a single sample (step 100). The optical signal for each trace is analyzed and based on a trace generation, in step 102, the base is called. An ASCII file is generated having the base sequence in step 104.

Alternatively, in step 106, the gel image can be constructed from the hyperspectral images. The gel image is the image cube where the depth in the wavelength dimension has been reduced to four, corresponding to the peak emission of each dye. The gel image can then be analyzed using conventional tracking and base-calling software (step 108).

An added feature of the present invention relates to the use of glass plates having linear surface profiles to help eliminate lane distortion or tracking errors during electrophoresis. One such plate-construction approach is to use a ruling engine similar to those used to make diffraction gratings to modify the gel plates. Such rulings would be very course by optical standards (less than 10 lines per millimeter). The ruled slab can be used as a master, for replicating the gratings to the desired optical specification of flatness and surface quality. The attractive features of capillary electrophoresis can thus be realized in a slab gel without the attendant problems of cleaning and reusing capillary glass components.

The wavelengths (488 nm and 514 nm) of the excitation light 42 from the argon ion laser 40 falls within the spectra range of the imaging spectrograph 54. Because the CCD camera 62 has a large dynamic range, the signal from the pixels associated with these wavelengths collect excitation light scattered from the gel 20. The scattered light may be monitored to track and calibrate the laser's optical power level. Further, because the fluorescence signal from the dyes is matched using deconvolution, the intensity spikes from the scattered excitation light do not interfere with calculating the weighting factors, thus avoiding the use of excitation light filters and external excitation light power monitors.

Optical Performance

As presently understood, a sequencing run on each of the 384 lanes of the slab gel requires about 12 nanograms of single stranded DNA template (M13 insert plus vector of ~8.2 kb). That sample size of $4.3 \times 10^{-15}$ mol or about $2.6 \times 10^9$ molecules of DNA provides a fluoresce signal that is roughly equal to the signal from background fluorescence and scattering. For identifying cosmids, this corresponds to 1440 nanograms of template DNA. For DNA sequencing, a typical DNA cycle sequencing reaction produces 1000 fragment lengths in the sequencing ladder. Fifteen rounds of extension at 80% efficiency are performed and each fragment is a terminated fluorochrome labeled molecule(primer or terminator). Accordingly, about $3.1 \times 10^7$ ($2.6 \times 0.10^9 \times 0.8 \times 15/1000$) of each fragment length is in each lane. An assumption that all fragment lengths are produced equally is true to about a factor of 2 to 4.

For a weak fluorophore, photo-bleaching occurs after about 3200 cycles. This will require $1.42 \times 10^{11}$ photons ($3.1 \times 10^7 * 3200/0.7$) at 70% quantum efficiency (Q.E.) in the read volume of each lane. At an excitation wavelength of 488 nanometers, a photon has an energy equal to hv, or $4 \times 10^{-19}$ joules/photQn. The total energy required to photobleach the weak fluorophore is $6 \times 10^{-8}$ joules of excitation light at a wavelength of 488 nm. This energy level establishes the maximum useful level of excitation light energy per lane. More specifically, $2.3 \times 10^{-5}$ joules ($384 * 6 \times 10^{-8}$) per read event for all 384 traces is the maximum excitation energy. If the gel is read 6 times a second, the total excitation energy required for each read is $1.4 \times 10^{-4}$ watts at a wavelength of 488 nm. A laser having an optical power level in the milliwatt range, to allow for inefficiencies, should thus be used.

The integrated fluorescence and Raman scatter from the gel/buffer are similar in magnitude. The gel background fluorescence is about equivalent to $2 \times 10^{-10}$ mol of fluorescein when excited at 488 nm. Accordingly, the gel/buffer produces about $8 \times 10^9$ photons/steradian (sr) ($0.7 \cdot 1.42 \times 10^{11}/4\pi$) for a single read of a lane. In the apparatus of the present invention, the total Raman and gel fluorescence background radiance, $L_{bk}$, has been found to be about twice this value or $1.6 \times 10^{10}$ photons/sr.

The fluorescent signal level can be calculated as the number of incident photons times the quantum efficiency of the dye. Dye quantum efficiencies vary widely. Ethidium bromide has a Q.E. of about 15% while SYBR Green 1 has a Q.E. of about 80%. An intermediate Q.E. value of 50% will be used for this calculation. Accordingly, a typical signal level will be $7.1 \times 10^{10}$ photons ($0.5 \cdot 1.42 \times 10^{11}$)into $4\pi$ steradian, or a signal radiance, $L_s$, of $7.15 \times 10^{10}/4\pi = 5.65 \times 10^9$ photons/sr based on the maximum excitation level established above for photo-bleaching.

Therefore, the contribution of the background fluorescence and Raman scattering ($8 \times 10^9$ photons/sr) is approximately equal to the signal from the fluorescent dyes ($5.65 \times 10^9$ photons/sr). This background level, in conjunction with a camera that has 12 to 14 bit resolution (2048 to 16,384 counts of intensity resolution) gives more than an adequate signal for deconvolution, peak finding, and ultimately, base calling.

Signal-to-Noise Ratio

The calculation of the SNR of the optics and associated systems demonstrates that the signal detection noise is small. The signal detection noise is different from the background noise because the background noise can be subtracted away, but the signal detection noise appears as an undesirable signal component inherent in all detection devices.

The SNR for each lane of the slab gel may be written as:

$$SNR = N_s / (\Sigma N_n^2)^{1/2}$$

where $N_s$ is the signal count and ($\Sigma n_n^2$) is the sum of the square of the noise counts. For the SNR Calculation, the following definitions apply:

$\Omega$=solid angle subtended by the collecting optics (steradian)

t=transmission of optics (fraction)

$\xi$=quantum efficiency of detector (electrons/photon)

$\tau$=integration time on the CCD detector n=number of spectral pixels per lane on the CCD Accordingly $N_s$ is as follows:

$N_s = \Omega \tau \xi L_s / n$ electrons/pixel and $\Sigma N^2_n = n N_{dk}^2 + N_{bk} + n N_{rd}^2 + N_s$ where:

$N_s$=the signal count, defined above (electrons)

$N_{dk}$=pixel dark noise (RMS electrons)

$N_{rd}$=pixel read noise (RMS electrons)

$N_{bk}$=background count=$\Omega \tau \xi L_{bk}$ (electrons)

For the signal and background counts, the root of the mean value is taken to represent the variance of a normal distribution, and hence the noise.

As discussed above, a suitable scientific CCD detector for use with the invention is available from Scientific Imaging Technologies, Inc., model S1424A, as a 2048×2048 camera. The camera's detector plane has 2048 pixels oriented to the spatial direction, and 2048 pixels to cover the spectral dimension. The pixels are $24\mu \times 24\mu$ square and are binned in the spectral dimens 58 to better match the point spread function of the spectrograph. Hence, the spectra are sampled into 256 pixels, these pixels containing all the detected photoelectrons emitted by the fluorophore's light. The spatial dimension 60 has 2048 elements to resolve the 384 lanes. Of course, the lanes can always be widened to, for example, 96 lanes across the gel, and proportionately more pixels would cover each lane.

The pixel read noise is an inverse function of the readout rate (1 MHz). With the pixels binned 8x on the CCD chip of the camera 62, there are $5.2 \times 10^5$ values to be read. Accordingly, the value of $N_{rd}$ is:

$N_{rd}$=5 rms electrons

A typical dark current at $-30°0$ C. is 1 e-/sec/pixel. With a binning of 8 pixels and sampling of the read area with $1/\tau$ frames per second, then:

$N_{dk} = 8 \cdot \tau$ (electrons)

For this calculation, $\tau$ was 0.17 seconds, the optical efficiency, t, for the camera 62 was 0.3, and the quantum efficiency, $\xi$, was 0.45.

With the S1424A CCD chip, the spatial dimension 60 of the image plane 56 is nearly 49 mm square. The imaging spectrograph 54 is designed with a focal image plane 56 sufficiently large to accommodate the large focal plane of the CCD chip with a focal ratio of f/4.0. The instrumental magnification is unity, and the gel slab 20 has 384 lanes 18 in a total width of 150 mm resulting in the magnification onto the slit being 48/150=0.32. The field-of-view of the spectrograph 54 is only 0.2 radians. The derived solid angle $\xi$ is: $\xi = (\pi 37.5^2/4)/750^2 = 1.96 \times 10^{-3}$ steradians, where 750 millimeters is the distance between the spectrograph's foreoptics and the gel surface.

Single Pixel SNR

The SNR is calculated using the above assumptions. Before performing spectral correlations with the known emission spectral signatures of the fluorescent markers, it is advantageous to have an adequate SNR at the pixel level of the CCD camera 62. To determine the available SNR at the pixel level, a worst case scenario is assumed where the emission spectra to be detected is uniformly distributed across all 256 continuous and contiguous spectral binned pixels, and then solve for the SNR.

$$SNR_{single\ pixel} = 7.5 = 17.5 dB$$

A SNR of 17.5 dB is sufficiently robust to allow a high detection probability. Further, the CCD camera 62 has sufficient dynamic range because the calculated signal counts are $5.8 \times 10^3$ electrons and the well pixel (or CCD) capacity of the CCD chip is $2.0 \times 10^5$ electrons.

Two assumptions are made in the above analysis. The first assumption involves the range of fragment lengths of single stranded DNA. Each length was assumed to be produced in equal numbers by the endonuclease restriction processes. Actually, smaller strands are statistically more likely to be produced than the longer fragments. This assumption overpredicts the SNR achievable on the longer fragments.

The second assumption is that the fluorescent spectrum of the fluorophores is uniform across the spectral response of the imaging spectrograph 54. The spectral features have a wide dynamic range and normally fail to utilize the entire spectral range of the instrument. Hence, the single pixel SNR is a spectral variable of wide dynamic range that is greatly underestimated.

The frame rate required of the CCD camera 62 is determined by the rate of migration of the fragments across the read zone 28 of the gel 20. Frame rates of the present embodiment are less than 6 per second and can be much lower. The CCD's frame rate determines the laser power required. If the CCD frame rate is low, then the excitation energy can be applied over a longer period of time for a lower average laser power. One skilled in the art would recognize that, in practicing the present invention, a number of trade offs exist between data rate, read noise, dark noise, data processing speeds and data storage.

Spectral Correlation

The correlation is performed in software, not on the CCD chip. Stored templates of all known fluorophores are compared against each unknown measured complete spectra. This allows wide versatility in the selection and number of dyes used in any run. The calculated values for a perfect correlation yields a SNR of 1,923, or 65 dB. This value is found by substituting unity for the number of pixels, n, in the numerator in the signal count equations discussed above. With this performance, the probability of detecting and correctly identifying a fluorescent marker is essentially unity and the probability of an error is very small.

If more than one fluorophore terminator is present during the CCD signal integration time, these can be spectrally un-mixed using software that uses the limited number of spectra used in the experiment. This library of possible spectra is referred to in hyper-spectral image processing as "end-members". End-members are used linearly to determine the fraction of each which yields the minimum "residual"—the portion of the signal not attributed to a specific spectrum, usually noise. Hence, with spectral pixel un-mixing, more than one fluorophore may be detected and read during a single read.

The unmixing is solved using the equation:

$$I(\lambda) = \Sigma a_N f_N(\lambda)$$

where:
N=number of dyes, $f_N(\lambda)$=the spectral emission of the dyes, $a_N$=the spectral contribution of the dye or "weighting" factor and is found by deconvolution of I ($\lambda_2 < \lambda < \lambda_1$) ($\lambda_2$=450 nm, $\lambda_1$=900 nm).

As is shown above, the instrumentation noise level is orders of magnitude smaller than the "biological" noise level for the sequencing sample. The typical amount of biological noise (sometimes called background by sequencing technicians) in the traces for existing machines varies greatly depending on the success of the cycle-sequencing reaction, which in turn depends on the sequencing target, and the quality and quantity of the target DNA preparation. In a sequencing cycle, the sample or biological noise can vary from about a few percent to ≈70% and still the base-calling software of the invention performs well. This level is significantly above the 0.05% contribution by the instrument (i.e. 65 db SNR).

Advantageously, a DNA sequencer of the present invention has the capability of sequencing 76,800 base pairs per hour. This rate is 5 to 30 times faster than existing DNA sequencers.

While the invention herein disclosed has been described by means of specific embodiment and applications thereof, numerous modification and variations could be made thereto by those skilled in the art without departing from the scope of the invention set forth in the claims.

What is claimed is:

1. Apparatus for detecting charged molecules having differing mobilities and chemical properties and having fluorescent tags, each tag corresponding to a particular chemical property of the molecules, comprising:

a plurality of electrophoresis lanes, each lane having a respective first and second end, and an electrophoresis medium between the first and second end of each lane, wherein an electrical potential, of appropriate polarity, is applied between the first and second end causes the charged molecules, applied at the first end, to travel toward the second end at a rate proportional to the molecule's mobility such that the charged molecules are separated along the lane based on the molecules mobility;

a read zone that extends substantially along an image line that intersects the plurality of electrophoresis lanes near the second ends;

a light source that illuminates the read zone with excitation light to cause the charged molecules to fluoresce producing fluorescent light; and a hyperspectral imager that spectrally images the fluorescent light onto a two-dimensional imaging plane, the first dimension being associated with a distance along the image line of the read zone and the second dimension being associated with the wavelength of the fluorescent light, the hyperspectral imager having continuous channels less than about 5 nanometers wide and including means for providing a spectral resolution of about 3–4 nanometers, contiguously spaced between about 450 nanometers and 900 nanometers.

2. Apparatus for detecting fluorescent molecules as defined in claim 1, further comprising:

a camera having a two dimensional pixel array, the camera generating video signals based on the intensity of light incident upon the pixel array.

3. Apparatus for detecting fluorescent molecules as defined in claim 1, wherein:

the hyperpsectral imager further comprises a linear entrance aperture with discrete locations along the aperture corresponding to locations along the first dimension of the image plane; and the apparatus further comprises a plurality of optical fibers that couple the fluorescent light from the read zone to corresponding locations along the entrance aperture.

4. Apparatus for detecting fluorescent molecules as defined in claim 1, wherein the hyperspectral imager includes an optical lens system that directly images the read zone.

5. Apparatus for detecting fluorescent molecules as defined in claim 1, further comprising a processor that compares the detected fluorescent light received from molecules of a given mobility with reference spectral profiles for the fluorescent tags, to identify the associated fluorescent tag and thus the molecule's associated chemical property.

6. Apparatus for detecting fluorescent molecules as defined in claim 5, wherein:

the charged molecules are at least 10 differing genetic markers of a genome;

a fluorescent tag, having a unique spectral profile, is associated with each genetic marker; and the processor compares the detected fluorescent light with the reference spectral profiles by calculating weighting factors f or each reference spectral profile based on a deconvolution of the detected fluorescent light with the reference spectral profile for each of the fluorescent tags.

7. Apparatus for detecting fluorescent molecules as defined in claim 5, wherein:

at least one fluorescent dye is attached to charged molecules of a known mobility, to provide a mobility calibration reference; and the processor calculates the mobility of any charged molecules of unknown mobility, based on the unknown molecule's travel rate and the mobility calibration reference.

8. Apparatus for detecting fluorescent molecules as defined in claim 5, wherein:

the fluorescent tags used in adjacent lanes differ from each other; and the processor tracks lane drift along the image line using the difference between the fluorescent tags in adjacent lanes.

9. Apparatus for detecting fluorescent molecules as defined in claim 5 wherein at least one additional fluorescent tag is used in every other lane.

10. Apparatus for detecting fluorescent molecules as defined in claim 9 wherein four fluorescent tags are used in each lane to identify the bases C, G, A and T, respectively, of a DNA fragment, and wherein a fifth fluorescent tag is added to every second lane for use in lane tracking.

11. Apparatus for detecting fluorescent molecules as defined in claim 1, further comprising a display that displays a graph of the chemical property of the molecules crossing the imaging line verses time.

12. Apparatus for detecting fluorescent molecules as defined in claim 1, wherein the charged molecules are DNA fragments, each fragment being tagged with an attached fluorescent dye that identifies the fragment's end base.

13. Apparatus for detecting fluorescent molecules as defined in claim 1, wherein the fluorescent tags are four primer dyes, FITC, TRITC, NBD-fluoride, and Texas Red, corresponding to the bases C, G, A, and T, respectively.

14. Apparatus for detecting fluorescent molecules as defined in claim 1, wherein the light source generates excitation light at wavelengths of about 488 nanometers and 514 nanometers.

15. Apparatus for detecting fluorescent molecules as defined in claim 1, wherein:

the lanes are on a planar substrate;

the excitation light is a laser beam that travels along the image line to simultaneously illuminate the lanes.

16. Apparatus for detecting fluorescent molecules as defined in claim 15, further comprising a mirror that reflects the laser beam back through the read zone along the image line to increase the intensity and uniformity of the fluorescent light.

17. Apparatus for detecting fluorescent molecules as defined in claim 15, further comprising a lens that couples the laser beam from a laser to the gel to increase the intensity of the excitation light traveling along the image line.

18. Apparatus for detecting fluorescent molecules as defined in claim 1, further comprising:

optical fibers for coupling the fluorescent light from the image line to an entrance slit on the imaging spectrometer;

a cylindrical lens that focuses the fluorescent light from the imaging line onto ends of the optical fibers; and a mirror located behind the read zone such that fluorescent light travelling away from the fiber end is reflected back toward the optical fiber ends.

19. Apparatus for detecting fluorescent molecules as defined in claim 1, wherein the second dimension of the imaging plane corresponds to the spectral range from about 450 nanometers to about 900 nanometers.

20. Apparatus for detecting fluorescent molecules as defined in claim 1, wherein:

the excitation light is narrowband light having a wavelength within a spectral range of the imaging spectrometer such that excitation light scattered by the electrophoresis gel is imaged on a pixel array on the imaging plane;

the electrical signals, generated by the-pixel array based on the intensity of light collected by pixels of the pixel array corresponding to the wavelength of the excitation light, provide a monitor of the excitation light's intensity.

21. Apparatus for detecting fluorescent molecules as defined in claim 1, further comprising a buffer to optically couple the light from the light source to electrophoresis medium.

22. Apparatus for detecting fluorescent molecules as defined in claim 1, further comprising first and second electrodes for applying the electrical potential to the lanes at the first and second ends, respectively, and extending across all of the plurality of lanes.

23. Apparatus for detecting fluorescent molecules as defined in claim 22, further comprising a plurality of loading electrodes situated near the first electrode, each loading-electrode associated with a lane for loading the charged molecules into the lanes.

24. Apparatus for detecting fluorescent molecules as defined in claim 1, wherein the electrophoresis medium is a gel having a thickness of 200 microns which is sandwiched between two glass plates.

25. Apparatus for detecting fluorescent molecules as defined in claim 1, wherein the read zone further includes fluorescent markers at each end of the image line for indicating the read zone.

26. Apparatus for detecting fluorescent molecules as defined in claim 1, wherein the plurality of electrophoresis lanes comprise 384 separate parallel lanes.

27. Apparatus for detecting fluorescent molecules as defined in claim 1, wherein the hyperspectral imager simultaneously images the fluorescent light onto the two-dimensional imaging plane without any scanning motions or delays.

28. Apparatus for detecting fluorescent molecules as defined in claim 1, wherein the plurality of electrophoresis lanes comprise a capillary electrophoresis array.

29. Apparatus for detecting fluorescent molecules as defined in claim 1, further comprising a heater that is thermally coupled to the electrophoresis medium for maintaining the medium within a predetermined temperature range.

30. A method for sequencing DNA, comprising:

producing DNA fragments that are tagged with fluorescent dyes, the dyes indicating an end base associated with the respective DNA fragment;

separating the DNA fragments according to mobility using electrophoresis of the fragments on a plurality of electrophoresis lanes, the separated DNA fragments forming fragment groups of slightly different mobility;

exciting the fragment groups with excitation light to cause the fluorescent tags to fluoresce;

forming a series of hyperspectral images of the separated DNA fragments, the hyperspectral images simultaneously covering all of the electrophoresis lanes and a broad spectral range; and identifying the fluorescent dye associated with DNA fragments of particular molecular weight by fitting the spectra emitted by a fragment group with reference spectra associated with the fluorescent dyes.

31. Apparatus for detecting charged molecules having differing mobilities and chemical properties and having fluorescent tags, each tag corresponding to a particular chemical property of the molecules, comprising:

a plurality of electrophoresis lanes, each lane being on a planar substrate and having a respective first and second end, and an electrophoresis medium between the first and second end of each lane, wherein an electrical potential, of appropriate polarity, is applied between the first and second end causes the charged molecules, applied at the first end, to travel toward the second end at a rate proportional to the molecule's mobility such that the charged molecules are separated along the lane based on the molecule's mobility;

a read zone that extends substantially along an image line that intersects the plurality of electrophoresis lanes near the second ends;

a laser source that illuminates the read zone with a laser beam along the image line to simultaneously illuminate the lanes, causing the charged molecules to fluoresce producing fluorescent light;

a mirror that reflects the laser beam back through the read zone along the image line to increase the intensity and uniformity of the flourescent light; and an imaging spectrometer that spectrally images the fluorescent light onto a two-dimensional imaging plane, the first dimension being associated with a distance along the image line of the read zone and the second dimension being associated with the wavelength of the fluorescent light.

32. Apparatus for detecting charged molecules having differing mobilities and chemical properties and having fluorescent tags, each tag corresponding to a particular chemical property of the molecules, comprising:

a plurality of electrophoresis lanes, each lane having a respective first and second end, and an electrophoresis medium between the first and second end of each lane, wherein an electrical potential, of appropriate polarity, is applied between the first and second end causes the charged molecules, applied at the first end, to travel toward the second end at a rate proportional to the molecule's mobility such that the charged molecules are separated along the lane based on the molecule's mobility;

a read zone that extends substantially along an image line that intersects the plurality of electrophoresis lanes near the second ends;

a light source that illuminates the read zone with excitation light to cause the charged molecules to fluoresce producing fluorescent light;

an imaging spectrometer that spectrally images the fluorescent light onto a two-dimensional imaging plane, the first dimension being associated with a distance along the image line of the read zone and the second dimension being associated with the wavelength of the fluorescent light;

optical fibers for coupling the fluorescent light from the image line to an entrance slit on the imaging spectrometer;

a cylindrical lens that focuses the fluorescent light from the imaging line onto ends of the optical fibers; and a mirror located behind the read zone such that fluorescent light travelling away from the fiber end is reflected back toward the optical fiber ends.

33. Apparatus for detecting charged molecules having differing mobilities and chemical properties and having fluorescent tags, each tag corresponding to a particular chemical property of the molecules, comprising:

a plurality of electrophoresis lanes, each lane having a respective first and second end, and an electrophoresis medium between the first and second end of each lane, and further comprising first and second electrodes situated to apply an electrical potential to the lanes at the first and second ends, respectively, wherein an electrical potential, of appropriate polarity, applied between the first and second electrodes causes the charged molecules, applied at the first end, to travel toward the second end at a rate proportional to the molecule's mobility such that the charged molecules are separated along the lane based on the molecule's mobility;

a plurality of loading electrodes situated near the first electrode, each loading electrode being associated with a lane for loading the charged molecules into the lanes;

a read zone that extends substantially along an image line that intersects the plurality of electrophoresis lanes near the second ends;

a light source that illuminates the read zone with excitation light to cause the charged molecules to fluoresce producing fluorescent light; and an imaging spectrometer that spectrally images the fluorescent light onto a two-dimensional imaging plane, the first dimension being associated with a distance along the image line of the read zone and the second dimension being associated with the wavelength of the fluorescent light.

34. A method for detecting and sequencing charged molecules having differing mobilities and chemical properties, the charged molecules being fragments of a larger molecule and the detection thereof permitting sequencing of the larger molecule, the method comprising:

tagging the respective fragments with flourescent dyes, the dyes indicating an end base associated with the respective fragment;

separating the fragments according to mobility using electrophoresis of the fragments on a plurality of electrophoresis lanes, the separated fragments forming fragment groups of slightly different mobility; illuminating a read zone associated with each electrophoresis lane with an excitation light source as the fragments pass therethrough, the excitation light source causing the charged molecules to fluoresce producing fluorescent light; and hyperspectrally imaging the fluoresced light onto a series of two-dimensional planes, the hyperspectral images thus formed simultaneously covering all of the electrophoresis lanes and a broad spectral range.

35. The method of claim 34 wherein the step of hyperspectrally imaging comprises forming a hyperspectral image having a first dimension associated with a distance along an image line of the read zone and a second dimension associated with the wavelength of the fluoresced light, and further having continuous channels less than about 5 nanometers wide and having a spectral resolution of about 3–4 nanometers, continuously spaced between about 450 nanometers and 900 nanometers.

36. The method of claim 34 wherein the charged molecules which are grouped into respective fragments comprise DNA fragments.

37. The method of claim 34 further including identifying the fluoresced light with a dye associated with DNA fragments of particular molecular weight by fitting the spectra emitted by a fragment group with reference spectra associated with fluoresced light from a reference dye.

* * * * *

UNITED STATES PATENT AND TRADEMARK OFFICE
CERTIFICATE OF CORRECTION

PATENT NO. : 5,871,628
DATED : February 16, 1999
INVENTOR(S) : Ali Dabiri, et al.

It is certified that error appears in the above-identified patent and that said Letters Patent is hereby corrected as shown below:

<u>IN THE CLAIMS</u>: In Claim 20, column 18, line, 1, change "the-pixel" to --the pixel--. In Claim 23, column 18, line 17, delete hyphen after "loading-". In Claim 31, column 19, line 4, change "causes" to --causing--. In Claim 32, column 19, line 34, change "causes" to --causing--. In Claim 33, column 20, line 5, change "causes" to --causing--. In Claim 34, column 20, actual line 37 (apparent line 39), after "mobility;" begin a new paragraph with "illuminating". In Claim 35, column 20, actual line 54 (apparent line 56), change "continuously" to --contiguously--.

Signed and Sealed this

Seventeenth Day of August, 1999

Attest:

Q. TODD DICKINSON

*Attesting Officer*

*Acting Commissioner of Patents and Trademarks*

UNITED STATES PATENT AND TRADEMARK OFFICE
CERTIFICATE OF CORRECTION

PATENT NO. : 5,871,628
DATED : February 16, 1999
INVENTOR(S) : Dabiri, et al.

It is certified that error appears in the above-identified patent and that said Letters Patent is hereby corrected as shown below:

Column 5,
Line 62, replace the second occurrence of "an" with -- a --.

Column 6,
Line 36, after "lanes", insert a comma.
Line 53, after "38 is coupled", insert -- to --.
Line 64, after "particularly", insert a comma.
Line 65, after "nucleoproteins", delete the comma.

Column 9,
Line 42, delete "in".
Line 46, and line 49, replace "spacially" with -- spatially --.
Line 55, after "seen," insert -- that --.
Line 65, after "in", delete "a".

Column 10,
Line 1, replace "FIG." with -- FIGS. --.
Line 16, replace "FIGS." with -- FIG. --.

Column 12,
Line 44, insert a space after "molecule".

UNITED STATES PATENT AND TRADEMARK OFFICE
CERTIFICATE OF CORRECTION

PATENT NO. : 5,871,628
DATED : February 16, 1999
INVENTOR(S) : Dabiri, et al.

It is certified that error appears in the above-identified patent and that said Letters Patent is hereby corrected as shown below:

Column 13,
Line 13, insert a space before "into".

Column 15,
Line 3, replace "trade offs" with -- tradeoffs --.

Signed and Sealed this

Twenty-first Day of August, 2001

Attest:

*Nicholas P. Godici*

NICHOLAS P. GODICI
*Attesting Officer*   *Acting Director of the United States Patent and Trademark Office*